United States Patent [19]

Miljanich et al.

[11] Patent Number: 5,264,371
[45] Date of Patent: Nov. 23, 1993

[54] SCREENING METHOD FOR NEUROPROTECTIVE COMPOUNDS

[75] Inventors: George P. Miljanich, Redwood City; Robert S. Bitner, Mountain View; Stephen S. Bowersox, Menlo Park; James A. Fox, Palo Alto; Karen L. Valentino, San Carlos; Donald H. Yamashiro, San Francisco; Makoto Tsubokawa, South San Francisco, all of Calif.

[73] Assignee: Neurex Corporation, Menlo Park, Calif.

[21] Appl. No.: 855,269

[22] Filed: Mar. 23, 1992

Related U.S. Application Data

[60] Division of Ser. No. 561,766, Aug. 2, 1990, Pat. No. 5,189,020, which is a continuation-in-part of Ser. No. 440,094, Nov. 22, 1989, Pat. No. 5,051,403.

[51] Int. Cl.$^5$ .................. G01N 33/567; G01N 33/68
[52] U.S. Cl. ........................................ 436/503; 436/86
[58] Field of Search ............................. 514/12, 13, 14; 530/324, 325, 326; 436/503, 86; 424/2.9

[56] References Cited

U.S. PATENT DOCUMENTS

| | | | |
|---|---|---|---|
| 4,447,356 | 5/1984 | Olivera et al. | 530/327 |
| 4,925,664 | 5/1990 | Jackson et al. | 424/537 |
| 5,051,403 | 9/1991 | Miljanich et al. | 514/12 |
| 5,189,020 | 2/1993 | Miljanich et al. | 514/13 |

OTHER PUBLICATIONS

Bean, B. P., "Classes of Calcium Channels in Vertebrate Cells," Annu. Rev. Physiol. 51:367–384 (1989).
Choi, D. W., "Calcium-mediated neurotoxicity: relationship to specific channel types and role in ischemic damage," TINS 11(10):465–469 (1988).
Gray, W. R., et al., "Peptide Toxins from Venomous Conus Snails," Ann. Rev. Biochem. 57:665–700 (1988).
Hamilton, S. L., and Perez, M., "Toxins that Affect Voltage-Dependent Calcium Channels," Biochem. Pharmacol. 36(20):3325–3329 (1987).
Jones, O. T., et al., "Localization and Mobility of $\omega$-Coonotoxin-Sensitive $Ca^{2+}$ Channels in Hippocampal CA1 Neurons," Science 224:1189–1193 (1989).
Marqueze, B., et al., "Characterization of the $\omega$-Conotoxin-Binding Molecule in Rat Brain Synaptosomes and Cultured Neurons," Mol. Pharmacol. 34:87–90 (1988).
Olivera, B. M., et al., "Neuronal Calcium Channel Antagonists. Discrimination between Calcium Channel Subtypes Using $\omega$-Conotoxin from Conus magus Venom," Biochem. 26:2086–2090 (1987).
Takemura, M., et al., "Distribution of the $\omega$-Conotoxin Receptor in Rat Brain. An Autoradiographic Mapping," Neuroscience 32:405–416 (1989).
Tsien, R. W., et al., "Multiple types of neuronal calcium channels and their selective modulation," TINS 11(10):431–438 (1988).

Primary Examiner—Jeffrey E. Russel
Attorney, Agent, or Firm—Carol A. Stratford; Peter J. Dehlinger

[57] ABSTRACT

A partially purified omega conotoxin binding protein is disclosed. The protein, either in partially purified form or in a synaptosomal preparation, is useful in identifying compounds for use in reducing neuronal damage related to an ischemic condition, such as stroke, in a human patient.

1 Claim, 12 Drawing Sheets

Fig. 1

```
         1           5          10          15          20          25          30
MVIIA    C  K  G  K  G  A  K  C  S  R  L  M  Y  D  C  C  T  G  S  C  -  R  -  S  G  K  -  C              A
MVIIB    C  K  G  K  G  A  S  C  H  R  T  S  Y  D  C  C  T  G  S  C  N  R  -  -  G  K  -  C              B
GVIA     C  K  S  X  G  S  S  C  S  X  T  S  Y  N  C  C  R  -  S  C  N  X  Y  T  -  K  R  C  -  -  Y     C
GVIIA    C  K  S  X  G  T  X  C  S  R  G  M  R  D  C  C  T  -  S  C  L  L  Y  S  N  K  -  C  R  R  Y     D
RVIA     C  K  P  X  G  S  X  C  R  V  S  S  Y  N  C  C  S  -  S  C  K  S  Y  -  N  K  K  C  G           E
SVIA     C  R  S  S  G  S  X  C  G  V  T  S  I  -  C  C  -  -  G  R  C  -  -  Y  R  G  K  -  C  T        F
TVIA     C  L  S  X  G  S  S  C  S  X  T  S  Y  N  C  C  R  -  S  C  N  X  Y  S  R  K  -  C  R           G
```

```
              1           5          10          15          20          25          30
GVIA     C  K  S  X  G  S  S  C  S  X  T  S  Y  N  C  C  R  S  C  N  X  Y  T  K  R  C  Y

```
           1           5              10              15              20          25
MVIIA      C  K  G  K  G  A  K  C  S  R  L  M  Y  D  C  C  T  G  S  C  R  S  G  K  C-NH₂
           └──────────────┘           └──┘           └──────────────┘
FRAGMENTS
160                                   C           C  C  T  G  S  C  R  S  G  K  C-NH₂
                                      └──────────────────────────────┘
161                                C  S  R  L  M  Y  D  C  C  T  G  S  C-NH₂
                                   └────────────────────┘•
162        C  K  G  K  G  A  K  C•                       C  R  S  G  K  C-NH₂
           └──────────────┘                              •
163        C  K  G  K  G  A  K  C  S  R  L  M  Y  D  C  C-NH₂
           └──────────────┘                           •
170        C  K  G  K  G  A  K  C  S  R-NH₂
           └──────────────┘
171        C  K  G  K  G  A  K  A  S  R  L  M  Y  D  A  C-NH₂
172        C  K  G  K  G  A  K  C  S  R  L  M  Y  D  C  C-NH₂
           └──────────────┘                           •
173        C  K  G  K  G  A  K  C  S  R  L  M  Y  K  C-NH₂
           └──────────────┘                        •
174        A  K  G  K  G  A  K  A  S  R-NH₂
175        C  K  G  K  G  A  K  A                          A  R  S  G  K  C-NH₂
           └──────────────────────────────────────────────┘
176        C  K  S  K  G  S  K  A                          A  R  S  G  K  C-NH₂
           └──────────────────────────────────────────────┘
179        C  K  G  X  G  A  K  A  S  X  L  M  Y  D  A  C-NH₂
           └──────────────────────────────────────────────┘
```

Fig. 2

A: 0 nM SNX-124; 1000 nM Nifedipine
B: 10 nM SNX-124
C: 50 nM SNX-124
D: 200 nM SNX-124

A: Control
B: 100 nM SNX-111
C: 200 nM SNX-111
D: 330 nM SNX-111

SCREENING METHOD FOR NEUROPROTECTIVE COMPOUNDS

This is a division of application Ser. No. 07/561,766, filed Aug. 2, 1990, now U.S. Pat. No. 5,189,020, which is a continuation-in-part of application Ser. No. 440,094, filed Nov. 22, 1989, now U.S. Pat. No. 5,051,403.

FIELD OF THE INVENTION

The present invention relates to an omega-conotoxin binding protein, and to a method of selecting neuroprotective compounds based on compound binding affinity to the protein.

REFERENCES

Ahmad, S. and Miljanich, G., Brain Research 453:247-256 (1988).
Benveniste et al., J. Cereb. Blood Flow and Metabolism, 9, 629).
Bennett, J. P., et al., Neurotransmitter Receptor Binding, pp. 61-89, Raven Pres, N.Y. (1983).
Deshpande, J. K., Siesjo, B. K. and Wielock, T., J. Cereb. Blood Flow and Metabolism, 7:89 (1987).
Gray, W., Olivera, B., and Cruz, L., Annual Review of Biochemistry 57:665-700 (1988).
Greenberg, D. A., New Pharmacologic Strategies in Cerebral DN&P, 2(2), pp. 104-108 (1989).
Haley, T. and McCormick, W. Brit. J. Pharmacol. 12:12-15 (1957).
Kirino, T., Brain Research 239:57-69 (1982).
Newcomb, R. (1989), Liq. Chrom-Gas Chrom. 7:570-578.
Olivera, B., Mcintosh, J., Cruz, L., Luue, F., and Gray, W. (1984), Biochemistry 23:5087-5090.
Wauquier, A., Edmonds, H., Clincke, G. (1987), Neuroscience and Biobehavioral Reviews 11:287-306.
Yamaguchi, T. and Klatzo, I. in *Cerebral Ischemia* (Bes, A., Braquet, P. and Siesjo, B. K., eds.), Elsevier Science Publ., pp. 13-24 (1984).
Yamashiro, D., Int. J. Peptide Protein Res., 30, 9-12 (1987).

BACKGROUND OF THE INVENTION

Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

Both global and focal ischemic conditions have the potential for producing widespread neuronal damage, even if the ischemic condition is transient. Although some permanent neuronal injury may occur in the initial minutes following cessation of blood flow to the brain, most of the damage in global and focal ischemia occurs over hours or even days following the ischemic onset. Much of this neuronal damage is attributed to secondary consequences of reperfusion of the tissue, such as the release of vasoactive products by damaged endothelium, and the release of cytotoxic products (free radicals, leukotrienes, etc.) by damaged tissues.

Several drug strategies have been proposed for treatment of stroke and other neuronal conditions related to ischemia, and these have been reviewed in recent articles (e.g., Greenberg, Wauquier). Anti-coagulants, such as heparin, have been examined, but with mixed results. Similarly, antivasoconstriction agents, such as flunarazine, excitatory neurotransmitter antagonists, such as MK-801 and AP7, and anti-edemic compounds have shown mixed results, with no clear benefits to outweigh a variety of side effects, including neurotoxicity or increased susceptibility to infection.

Two general classes of vasodilators have been studied for possible treatment of neuronal ischemic damage. Non-specific vasodilators, including papaverine, prostacyclin, pentoxifylline, and nitroprusside failed to demonstrate nay clear benefit in reducing ischemic damage. A second general class of vasodilators includes a variety of calcium-antagonist vasodilator drugs. Verapamil and related compounds which prevent calcium entry into smooth and striated muscles appear to be effective only at high drug concentrations, where serious cardiotoxicity effects may ensue. Dihydropyridines, such as nimodipine, produced mixed results—some neurological improvement may be seen, but increased cerebral edema has also been observed Bensothiazepines, as exemplified by diltiazem, have shown moderate protective effects, but these drugs also appear to cause undesired side effects such as hypotension which may be inimical to treatment.

In summary, drugs which have been proposed to date for the treatment of stroke and other ischemic-related conditions of the brain are either (i) relatively ineffective, (ii) effective only at dosage levels where undesired side effects are observed, and/or (iii) produced systemic effects, such as hypotension, which comprise the potential effectiveness of the drug.

SUMMARY OF THE INVENTION

It is one object of the invention to provide a method for screening compounds for use in reducing neuronal damage related to an ischemic condition, such as stroke, in a human patient.

It is a related object to provide an omega conotoxin (OCT) binding protein in partially purified form.

In one aspect, the invention includes a partially purified OCT-binding protein derived from neuronal-cell synaptosomes, such as electric organ synaptosomes. The protein is characterized by:

(a) specific high affinity binding to MVIIA omegaconotoxins; and (b) a molecular weight, as measured by sodium dodecyl sulfate polyacrylamide gel electrophoresis, of about 210 Kd (kilodaltons).

The OCT-binding protein can be isolated, according to another aspect of the invention, by extracting a synaptosome preparation with digitonin, binding the extract material to wheat germ agglutinin agarose, eluting from the agarose a fraction having high MVIIA binding affinity, and separating the fraction by affinity chromatography, based on the binding of the purified calcium channel protein to an OCT, such as MVIIA.

The OCT-binding protein is used in a method for screening compounds for use in reducing neuronal damage due to an ischemic condition, such as stroke, in a human. The binding affinity of the compound to the OCT-binding protein can be measured in a synaptosomal preparation, or alternatively, in the partially purified protein, by competitive displacement of an OCT, such as MVIIA OCT. The test compound is selected if its binding affinity to the protein is at least as great as that of high-affinity MVIIA, MVIIB, GVIA, GVIIA, or RVIA OCT, and preferably as least as great as that of MVIIA or GVIA OCT.

In a preferred method, the compound is measured for its (i) binding affinity to the OCT-binding protein, and (ii) ability to inhibit voltage-gated calcium currents or neurotransmitter release in neuronal tissue. The compound is selected if its binding affinity to such binding protein, and its specific activity, in producing inhibition of such voltage-gated calcium currents or neurotransmitter release, is at least as great as that of high-affinity OCT peptides.

Also forming part of the invention is a method of reducing neuronal damage related to an ischemic condition in a human patient. The method includes administering to the patient, in a pharmaceutically acceptable amount, a compound effective to bind to an OCT-binding protein, with a binding affinity which is at least as great as that of high-affinity OCT peptides.

These and other objects and features of the invention will become more fully apparent when the following detailed description of the invention is read in conjunction with the accompanying drawings.

BRIEF DESCRIPTION OF THE DRAWINGS

FIG. 1 shows primary sequences of MVIIA, MVIIB, GVIA, GVIIA, RVIA, SVIA, and TVIA OCT peptides, indicated at A-G, respectively;

FIG. 2 shows the primary sequences of several OCT peptide fragments derived from the MVIIA OCT;

FIG. 3 shows the primary sequences of several OCT peptide fragments derived from the GVIA OCT;

DETAILED DESCRIPTION OF THE INVENTION

Figure 4A:
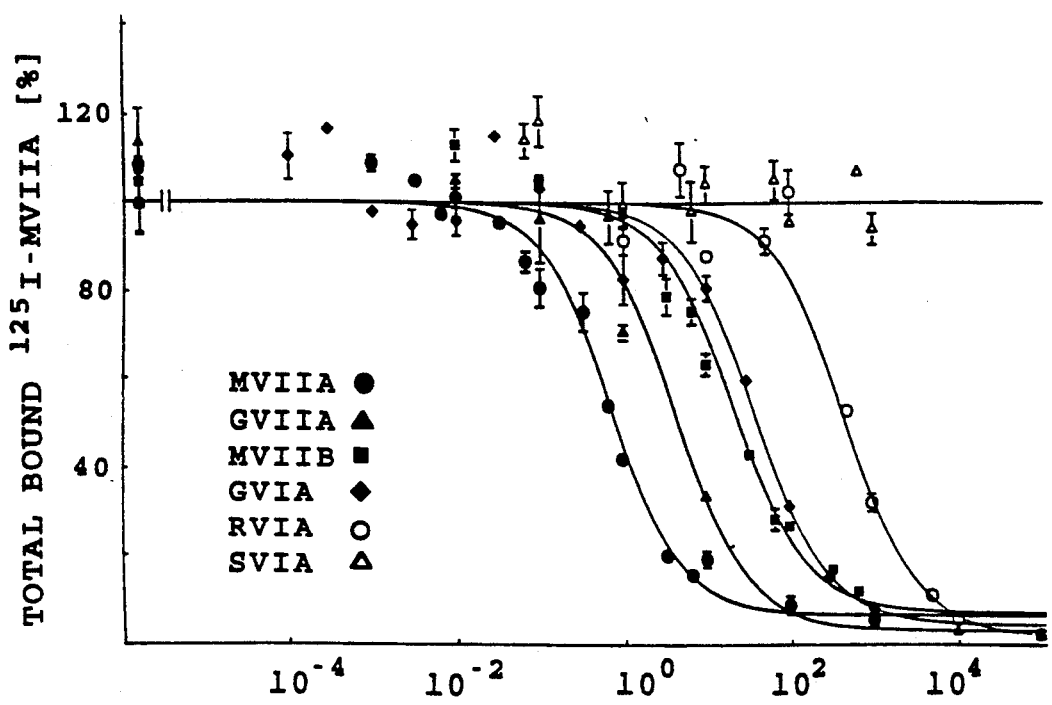
FIGS. 4A and 4B show computer-fit competitive binding curves for OCT peptide binding to electric-organ synaptosomes (4A), and rat brain synaptosomes (4B)

I. Preparation of OCT Peptides and Peptide Fragments

This section describes the synthesis, by solid-phase methods, of several naturally occurring omega conotoxin (OCT) peptides which are used in the present invention for characterizing the binding affinity of OCT-binding protein, and additional OCT peptides and peptide fragments which are screened in accordance with the method of the invention.

OCT peptides are peptide toxins produced by marine snails of the genus Conus, and which act as calcium channel blockers (Gray). About 300 species of cone snails in the Conus genus have been identified, and a variety of OCTs from several of these species have been isolated. The primary sequences of seven naturally-occurring OCT peptides which have been sequenced are shown at A-G in FIG. 1. Conventional letter initials are used for the amino acid residues, and X represents 4-hydroxyproline, also abbreviated 4Hyp. The peptides shown in the figure are amidated at their C-terminal ends.

The identifying names of the peptides are also given in the figure, and these names will be used herein to refer to the specific OCT peptide. For example, the peptide whose sequence is designated MVIIA will be referred to herein as MVIIA peptide, MVIIA OCT or simply MVIIA. The MVIIA and GVIA peptides also have the common names CmTx and CgTx, respectively.

The MVIIA and GVIA peptides are also shown in FIGS. 2 and 3, respectively, along with their three disulfide linkages, as demonstrated chemically or spectroscopically. All of the OCT peptides in FIG. 1 have these three linkages between the first and fourth, second and fifth, and third and sixth cysteine (Cys, C) residues.

The OCT peptides can be synthesized by a solid-phase synthesis method, such as that detailed in Example 1. Briefly, N-alpha-protected amino acid anhydrides are prepared in crystallized form and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1-2 reaction cycles are used for the first twelve residue additions, and 2-3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the ring.

The three disulfide linkages in the peptides may be formed by air oxidation in the presence of dithiothreitol (DTT) at room temperature or at 4° C. over an extended reaction period. Alternatively, where the correct or desired bridging cannot be achieved by random oxidation, a chemically directed process may be used in which the bridges are formed sequentially, one bridge at a time. The following side-chain protecting groups could be used for each pair of cysteine residues: 4-methylbenzyl, ethylcarbamoyl, and acetamidomethyl. These protecting groups constitute an orthogonal set in which any one kind of protecting group can be removed under conditions that do not affect the other two.

The strategy here involves removing one kind of protecting group from a pair of cysteine residues, followed by oxidation to form the first disulfide bridge. A second kind of protecting group is then removed, again followed by oxidation to form the second bridge. A third bridge, if needed, is formed in like manner. An example is the synthesis of compound No. 163 (with a bridge linking positions 1 and 16) followed by conversion to compound 172 (with the second bridge linking positions 8 and 15).

The peptide can be isolated by an initial separation by gel filtration, to remove peptide dimers and higher polymers, and also to remove undesired salts, such as guanidine hydrochloride, used in the oxidation reaction. The partially purified peptide is further purified by preparative HPLC chromatography, and the purity of the peptide confirmed by amino acid composition analysis. Details of the preparation and purification of the MVIIA peptide are given in Example 1A-1F, and for preparation and purification of the OCT peptides MVIIB, MVIIB, GVIA, GVIIA, RVIA, SVIA, and TVIA peptides, in Example 1G.

FIGS. 2 and 3 show portions of MVIIA and GVIA OCT peptides, respectively, which were prepared for peptide screening, in accordance with the method described in Section IV. A small dot below a Cys position indicates that the Cys residue is blocked (with an acetamidomethyl group) and therefore unable to participate in disulfide bridging. Thus for example, the peptide fragment labeled 160 extends between the third and sixth Cys residues corresponding to the C terminus of the full-length MVIIA peptide, and has a disulfide bridge between the third and sixth Cys, the fourth and fifth Cys residues being blocked. The peptide fragment labeled 162 includes a deletion between the positions 9 and 19, and is linked between the first and sixth Cys residues, the second and fifth Cys residues being blocked. The A, S, and X designations in the figure indicate Ala, Ser, and Hyp substitutions, respectively, at the positions shown.

The peptide fragments shown in FIGS. 2 and 3 were prepared substantially as described in Example 2, following the method detailed in Example 1, but using a single-coupling protocol.

II. OCT-Binding Protein

Co-owned U.S. patent application for "Method of Treating Ischemia-Related Neuronal Damage," Ser. No. 440,094 filed Nov. 22, 1989, now U.S. Pat. No. 5,051,403, describes a method of reducing neuronal damage related to ischemia, by administering OCT peptides which have certain binding and/or inhibitory properties. The properties which were found to be characteristic of active OCT compounds are (a) specific, high-affinity binding to synaptosomal preparations from fish electric organ or mammalian brain, (b) ability to inhibit calciumgated currents selectively in neuronal tissue, and (c) ability to inhibit neurotransmitter release selectively in neuronal tissue.

The binding affinity of OCT peptides for electric-organ and mammalian-brain synaptosomes was measured for OCT peptides A-F in FIG. 1. The synaptosomal membranes were prepared according to the procedures described in Examples 3A and 3B, and the binding affinities were measured according to the methods described in Example 4, and expressed either as binding constant $K_i$ values, or $IC_{50}$ values.

As detailed in Example 3A, the binding constant $K_d$ of MVIIA peptide for electric organ synaptosomes was determined by a saturation binding method in which increasing quantities of radiolabeled MVIIA were added the synaptosomes, and the amount of labeled material bound at each concentration was determined. The plot of bound peptide as a function of concentration was then used to calculate a $B_{max}$, the concentration of binding sites on the synaptosomes, and from this, the MVIIA binding constant $K_d$ for electric organ synaptosomes was calculated.

The binding constants $K_i$ of OCT peptides A-F were determined by competitive inhibition studies in which the concentration of test peptide required to displace half the bound, radiolabeled MVIIA peptide from the electric organ synaptosomes was determined. Competitive inhibition curves for the six OCT peptides examined are shown in FIG. 4A, where the symbols for the peptides are indicated in the figure. From the concentration needed to displace half the bound MVIIA peptide, and from the known $K_d$ value from MVIIA, the binding constant $K_i$ of each test peptide was determined. The method for calculating $K_i$ binding constants are detailed in Example 4A, and follow standard analysis methods (e.g., Bennett).

With reference to the competitive binding curves seen in FIG. 4A, and the calculated $K_i$ values in Table 1 below, OCT peptides MVIIA, GVIIA, MVIIB, GVIA, and RVIA all show specific, high affinity binding for the electric organ synaptosomes, as evidenced by a $K_i$ value of about 320 nM or less. These six OCT peptides are also referred to herein, collectively, as high-affinity OCT peptides. The $K_i$ value for the SVIA compound, by contrast, was at least about 1,000 fold greater than any of the high-affinity OCT peptides.

TABLE 1

| Compound | Ki (nM) |
| --- | --- |
| MVIIA | 0.44 |
| GVIIA | 3.1 |
| MVIIB | 13.2 |
| GVIA | 14.3 |
| RVIA | 324 |

TABLE 1-continued

| Compound | Ki (nM) |
|---|---|
| SVIA | >>100 µM |

Figure 4B:
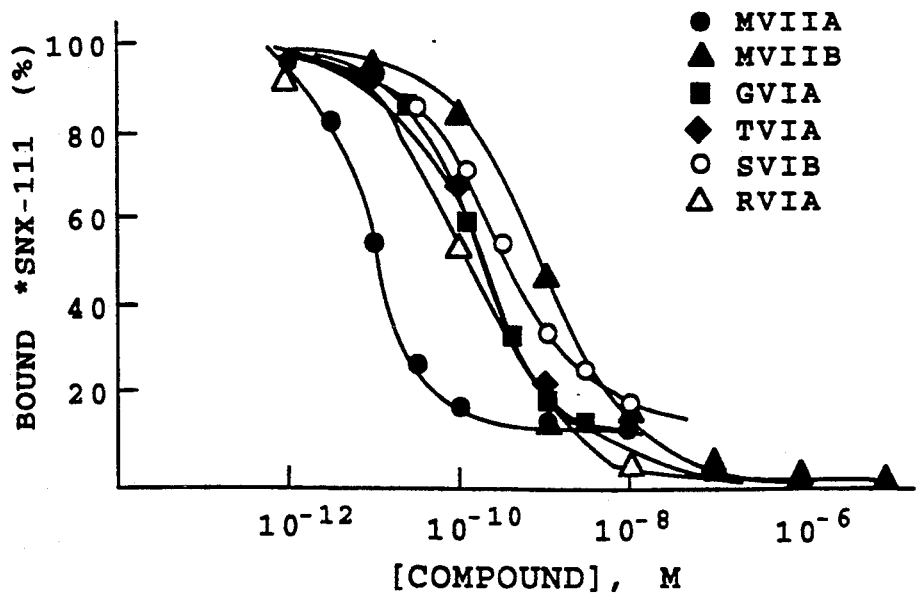

The binding affinities of the OCT compounds for rat brain synaptosomes were measured in terms of $IC_{50}$ values. These binding values were similarly determined from competitive binding studies with radiolabeled MVIIA. FIG. 4B shows concentration/displacement curves for the six test peptides, where the symbols for the peptides are shown in the figure. The calculated $IC_{50}$ values are shown in Table 2 below for $IC_{50}$ values determined under two different conditions, detailed in Example 4B. Peptides MVIIA, GVIIA, MVIIB, GVIA, and RVIA all show specific, high affinity binding to the rat brain synaptosomes, as evidenced by an $IC_{50}$ value of about 230 nM or less. The $IC_{50}$ for the SVIA compound, by contrast, was again at least about 1,000 fold higher than any of the other test OCT.

TABLE 2

| | BINDING | |
|---|---|---|
| COMPOUND | Rat Brain 1 ($IC_{50}$, nM) | Rat Brain 2 ($IC_{50}$, nM) |
| MVIIA | 0.019 | 0.010 |
| GVIA | 0.48 | 0.133 |
| MVIIB | 0.49 | 0.123 |
| GVIIA | 22.9 | nd |
| RVIA | 229.0 | 0.894 |
| SVIA | >1 mM | >1 mM | nd = not done

The binding affinity results above suggest that synaptosomes from neuronal cells contain an OCT-binding protein which is effective to bind high-affinity OCT peptides specifically. The identification of an OCT-binding protein from synaptosomal preparations was carried out using OCT peptide labeling and protein band fractionation by sodium dodecyl sulfate polyacrylamide gel electrophoresis (SDS-PAGE), as detailed in Example 5A. Briefly, $^{125}$I-MVIIA (SNX-111) or $^{125}$I-GVIA (SNX-124) were bound to electric-organ or rat-brain synaptosomes. After incubation in the presence or absence of unlabeled OCT peptide, the bound peptide was cross-linked to the synaptosomes by chemical crosslinking. The synaptosomes were then solubilized in SDS and fractionated by SDS-PAGE.

Figures 5A, 5B:
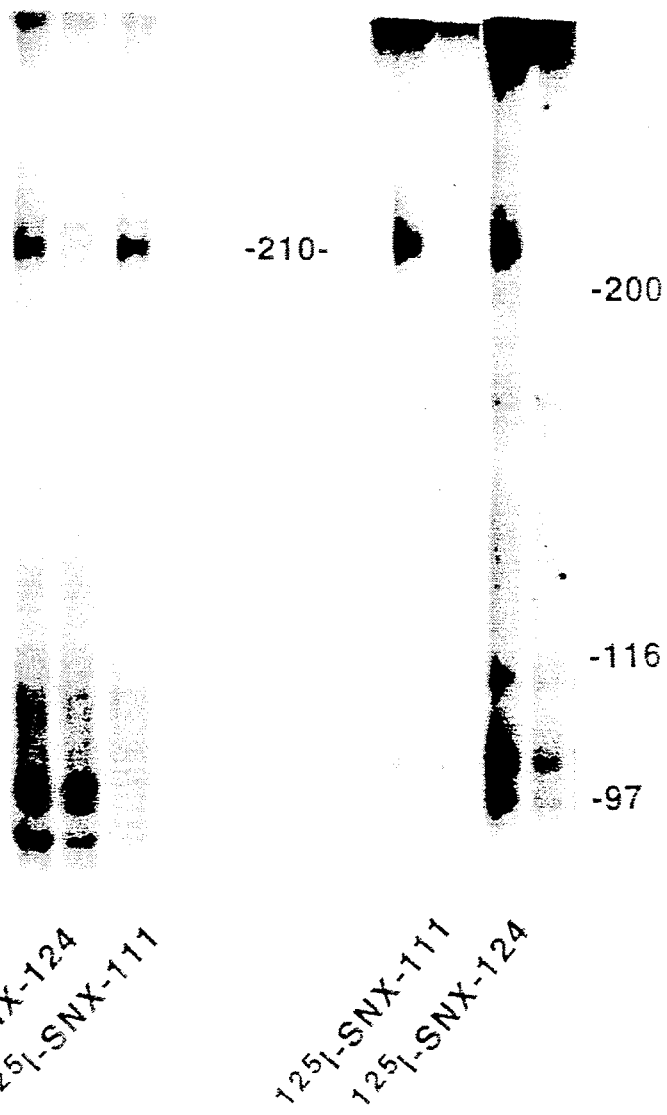
FIGS. 5A and 5B are SDS-PAGE electrophoretic patterns of MVIIA (SNX-111)- and GVIA (SNX-124)-labeled proteins from electric organ synaptosomes (5A), and rat brain synaptosomes (5B)

FIG. 5A shows the autoradiograms of SDS-PAGE gels observed for electric-organ synaptosomal membranes with bound GVIA (lanes 1 and 2) and MVIIA (lanes 3 and 4), where the membranes in lanes 2 and 4 were prepared in the presence of unlabeled OCT peptide. As seen from the gel patterns in lanes 1 and 3, both OCT peptides bound specifically to a protein with an approximate a molecular weight, as determined by its by its migration rate on SDS-PAGE, of about 210 Kd. As seen from the gel patterns in lanes 2 and 4, the OCT peptides were either substantially or completely displaced from this protein by excess, unlabeled OCT peptide. The upper band in the gels represents material which did not enter the gel. The lower labeled bands in the gels are apparently labeled non-specifically, since excess unlabeled OCT had little effect on the amount of labeling.

Similar results were obtained with MVIIA- and GVIA-labeled rat brain synaptosomes, as seen in FIG. 5B. The gel patterns show (a) specific labeling of a 210 kd protein by both OCT peptides, and non-specific labeling of other synaptosomal membranes.

Figure 6A:
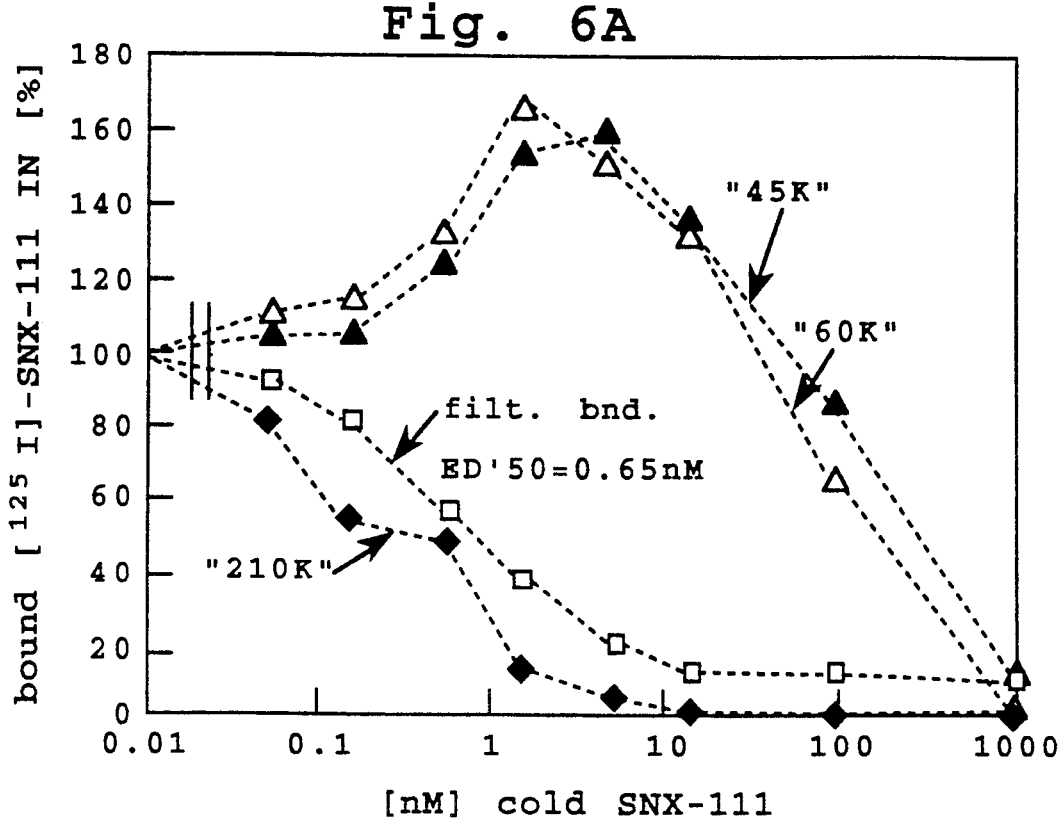
FIGS. 6A and 6B are plots showing the extent of radiolabeled MVIIA (SNX-111) displacement, as a function of concentration of unlabeled MVIIA (SNX-111), of 45 Kd, 60 Kd, and 210 Kd protein bands from electric-organ synaptosomes (6A), and rat brain synaptosomes (6B)

The specificity of the OCT binding to the 210 Kd protein was further examined by measuring the extent of MVIIA bound to the 210 Kd band, and to two lower-molecular-weight bands which show non-specific MVIIA binding, as a function of unlabeled MVIIA added to the synaptosomal preparation prior to cross-linking. Details of the study are given in Example 5B. FIG. 6A shows the results obtained with electric-organ synaptosomes. The plots show a sharp drop in amount of labeled MVIIA in the 210 Kd band, with an $EC_{50}$ (the amount of unlabeled MVIIA needed to displace half of the labeled MVIIA) of about 0.06 nM. A similar effect was observed for total synaptosomal membranes which were trapped on a membrane after cross-linking and extensive washing (open squares). These results support the finding that the MVIIA binding characteristics observed in synaptosomal preparations are due to OCT peptide binding to the 210 Kd protein in the preparation.

By contrast, the amount of labeled MVIIA associated with 45 Kd (closed triangles) and 60 Kd (open triangles) bands on the SDS-PAGE fractionation were not significantly reduced by unlabeled MVIIA at concentrations below about 50 nM, indicating non-specific OCT binding to these lower-molecular-weight proteins.

Figure 7:
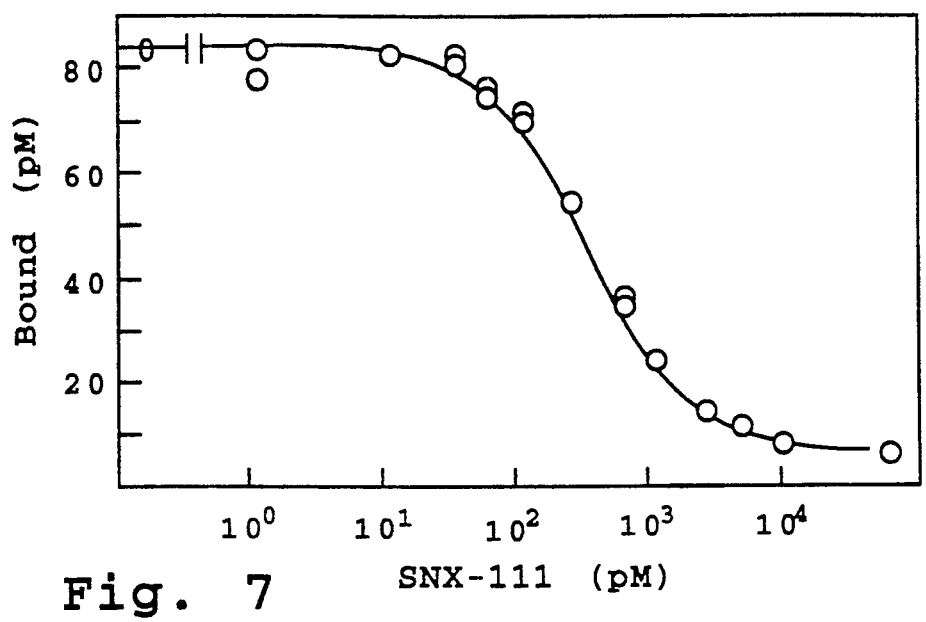
FIG. 7 is a displacement curve of radiolabeled MVIIA OCT by unlabelled MVIIA OCT (SNX-111) from solubilized, partially purified OCT-binding protein.

The 210 Kd OCT binding protein identified from the binding studies above can be partially purified in active form by the protein purification methods given in Example 6. Briefly, a synaptosomal preparation is extracted in an extraction solution containing digitonin and protease inhibitors. The solubilized material, which contains about 50–60% of the OCT binding protein, is isolated by centrifugation, and assayed for total amount of binding protein. The assay is performed as above, by measuring the displacement of radiolabeled MVIIA from the solubilized preparation, as a function of cold MVIIA added to the mixture. FIG. 7 shows a typical binding displacement curve for a digitoninsolubilized preparation, from which a $K_d$ binding constant of about 60.8 pM (picomolar) can be calculated. The molarity of the binding sites in the material can also be estimated from these experiments.

The solubilized material from above is mixed with wheat germ agglutinin (WGA) agarose, and the agarose with bound solubilized protein is poured into a column. The bound material is eluted, after washing, successively with 0.3M N-acetyl-D-glucosamine (NAG) and 0.3M NAG and 100 mM NaCl. The elution fractions are assayed for MVIIA binding, as above, and found to be associated predominantly with 0.3M NAG plus 100 mM NaCl elution fractions.

Figure 8:
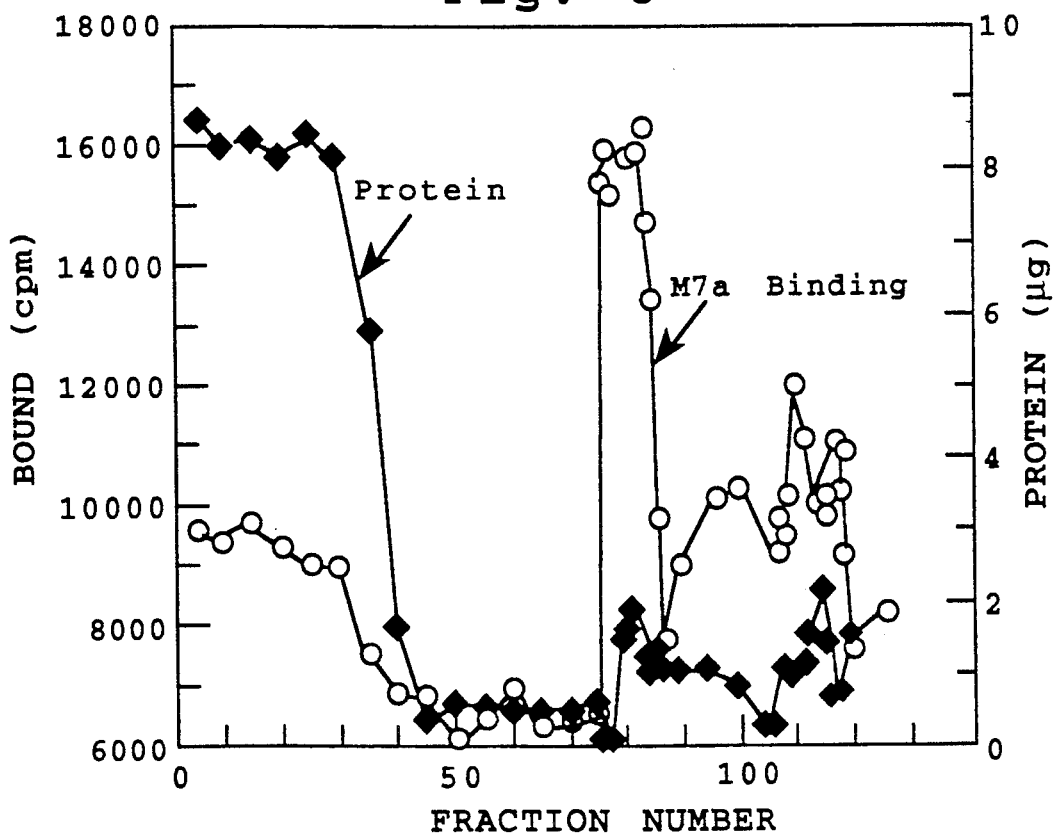
FIG. 8 is an elution profile of a synaptosomal fraction from an MVIIA affinity chromatography column, showing total labeled MVIIA counts (open circles) and protein content (closed diamonds)

The WGA agarose elution fractions are combined and applied to an MVIIA column material for affinity chromatography. The bound material on the affinity column is eluted, successively, with an elution buffer containing 0.5M NaCl and digitonin, pH 5.5, and the same buffer, at pH 11. The elution profile is shown in FIG. 8, where the open circles indicate the MVIIA binding activity of the fractions. The peak fractions eluting after first addition of salt are combined.

Table 3 below shows the enhanced purification at each step of the purification procedure, as measured by the specific MVIIA binding activity of the protein. As seen, the material obtained from the final affinity chromatography step has a specific activity of about 550 pmoles/mg, or about 550 times that of the OCT-binding protein in the original synaptosomal preparation.

TABLE 3

| Step | CA Antagonist pmol | Receptor % | Protein MG | Protein % | Specific Act. (pmol/mg) | X-Fold Purification |
|---|---|---|---|---|---|---|
| Crude Membranes | 11.04 | 100 | 9.2 | 100 | 1.2 | |
| Digitonin Extract | | 50–60 | | 50–60 | | |
| WGA-Agarose | 4.92 | 44.6 | 0.2 | 2.22 | 24.6 | 20 |
| MVIIA OCT Affinity | 0.66 | 6 | 0.001 | 0.111 | 660 | 550 |

III. Screening Method

In vitro and in vivo studies reported in the above-cited patent application for "Method of Treating Ischemia-Related Neuronal Damage," demonstrate a strong correlation between (a) high binding affinity to synaptosomal membranes, (b) inhibition of voltage-gated calcium ion currents and neurotransmitter release selectively in neuronal cells, and (c) ability to reduce neuronal damage in ischemia-related injury, such as stroke. The mechanism of neural protection by high-affinity OCT peptides presumably involves inhibition of voltage-gated calcium currents in neuronal membranes, thus blocking calcium influx into neuronal cells and the consequent release of neurotransmitters from the cells. This mechanism of OCT protection is consistent with the finding that neuronal damage in ischemia-related injury is associated with elevated intracellular calcium levels (Deshpande et al.).

In the present invention, it is further demonstrated that the OCT binding sites in neuronal membranes are present in a neuronal membrane protein having a molecular weight of about 210 Kd. This finding, combined with the finding that high-affinity OCT peptides inhibit voltage-gated calcium currents in neuronal cells, indicates that the OCT binding protein is a calcium channel protein which mediates voltage-gated influx of calcium ions into neuronal cells. This voltage-gated calcium influx is presumably associated with release of neurotransmitter(s) from the cell.

From the model above, it can be predicted that antagonistic compounds which have a high specific binding affinity to the OCT-binding protein will be effective inhibitors of voltage-gated calcium currents in neuronal cells, and that such compounds, in turn, are useful for reducing ischemia-related neuronal damage, such as caused by stroke. This model is the basis of the screening method of the invention.

In this method, a test compound is screened initially for its binding affinity to the neuronal membrane OCT binding protein. The binding affinity may be measured in intact neuronal membranes, in synaptosomes, or in the partially purified OCT-binding protein. In one preferred embodiment, the binding affinity is measured by competitive displacement of a high-affinity, radiolabeled OCT, such as radiolabeled MVIIA, from synaptosomal membranes, as described in Section II above. In another embodiment, the binding affinity is measured by competitive displacement of a high affinity, radiolabeled OCT peptide from a purified or partially purified OCT-binding protein. Alternatively, the binding of the compound to purified OCT-binding protein can be measured directly where the compound is radiolabeled or contains a moiety, such as a fluorescent group, which can be assayed in the bound state.

The test compound is classified as a high-affinity binding compound if its binding constant is within the range of binding affinities of the high-affinity OCT peptides MVIIA, MVIIB, GVIA, GVIIA, and RVIA.

Preferably, the compound binding affinity is within the range of the most active of the OCT peptides, particularly the MVIIA and GVIA OCT peptides.

Table 4 below shows the $K_i$ and/or $IC_{50}$ values measured for a number of OCT peptides, peptide fragments and lysine-peptides which are modeled after N-terminal peptide sequences in OCT peptides. Based on the measured binding affinities, OCT peptide TVIA, one MVIIA peptide fragment, designated 162, and the peptide pentalysine are identified as potential neuroprotective compounds, since all three peptides have binding affinities in the range of high-affinity OCT-binding peptides. The binding affinities of the test compounds were measured by the competitive inhibition method described in Example 4A or 4B.

TABLE 4

| COMPOUND | EOS ($K_i$, nM) | Rat Brain 1 ($IC_{50}$, μM) | Rat Brain 2 ($IC_{50}$) |
|---|---|---|---|
| TVIA | nd. | nd. | 0.310 nM |
| MVIIA 160 | 120. μM | 100.M | nd |
| MVIIA 161 | >>1. mM | .840 | >1. mM |
| MVIIA 162 | 170. | .505 | 12.4 μM |
| MVIIA 163 | 460. | 10. | nd |
| MVIIA 171 | 4600. | 3.4 | nd |
| MVIIA 172 | 21. μM | nd | nd |
| MVIIA 173 | 720. | 7.7 | 4. μM |
| MVIIA 174 | 530. | | nd |
| MVIIA 175 | 3600. | 250. | nd |
| MVIIA 176 | 1800. | 25. | nd |
| GVIA 177 | >>1. mM. | >>1 mM | nd |
| GVIA 180 | 123. μM | 187. | nd |
| KKKKK | 74. | nd | nd |
| KAKFKAR | 850. | nd | nd |
| KAKFKAH | 1.9 μM | nd | nd |
| KAKFKAQ | 23.4 μM | nd | nd |
| KAKFKAM | 34.3 μM | nd | nd |
| KAKFKAT | 85. μM | nd | nd |
| KAKFKAP | 106. μM | nd | nd |
| KAKFKAD | 1.74 mM | nd | nd |

Test compounds which show high-affinity binding to the OCT-binding protein may be additionally screened for inhibition of voltage-gated calcium channel currents and/or inhibiting neurotransmitter release selectively in neuronal cells. This secondary screen distinguishes high-affinity antagonistic compounds, which would act to produce the desired inhibition of voltage-gated calcium current and consequent inhibition of neurotransmitter release, from high-affinity agonists, which would have the opposite effect.

One suitable system for testing inhibition of neuronal calcium channel currents is the mouse neuroblastoma cell line, strain N1E115. Membrane currents are conveniently measured with the whole cell configuration of the patch clamp method, according to the procedure detailed in Example 7A. Briefly, a voltage clamp protocol is performed in which the cell potential was stepped from the holding potential of about −100 mV to test potentials that ranged from −60 mV to +20 mV, and the cell is held at the holding potential for 5 seconds between pulses.

Figure 9:
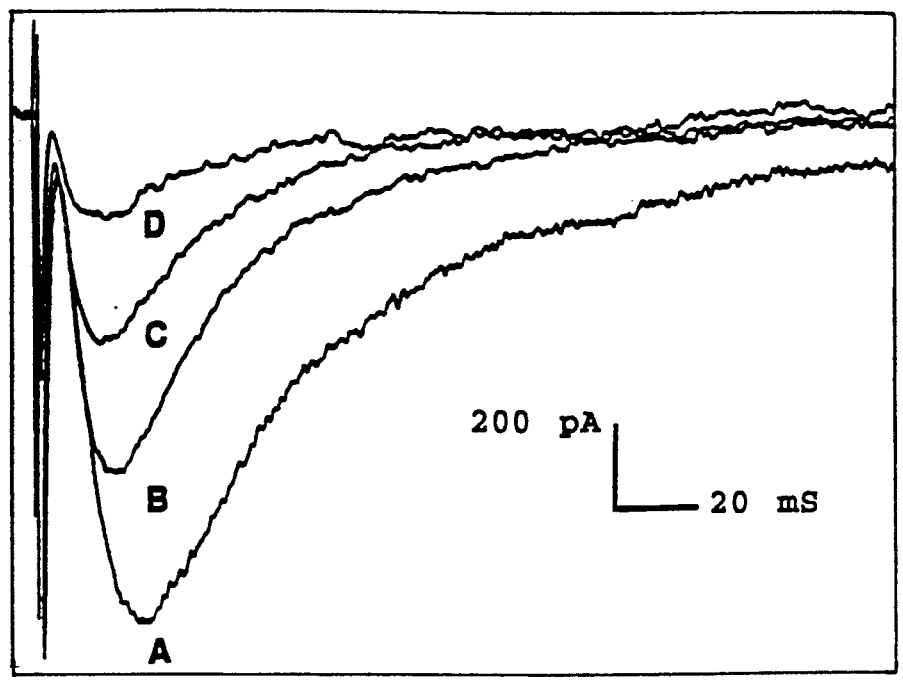
FIG. 9 shows voltage-gated calcium current traces induced by a voltage step from −100 or −80 mV to −20 mV in neuroblastoma cells treated with 1 μM nifedipine and no OCT peptide (trace A), and in neuroblastoma cells exposed to increasing concentrations of OCT peptide GVIA (SNX-124) in the absence of nifedipine (traces B-D)

FIG. 9, trace A, shows a typical inward calcium current elicited by a voltage step from −80 mV to −20 mV in the absence of OCT. As seen from the trace, the calcium current activate quickly (within about 20 ms) and inactivates with a time constant of 30 to 40 ms. The calcium current is measured by the amplitude of the peak inward current elicited by the depolarization peak and has a measured value of about −1196 pA. The cell in FIG. 9, trace A, was also exposed to 1 μM nifedipine, a dihydropyridine, which is expected to effectively block L-type calcium channels in the neuroblastoma cells. The calcium current observed is thus expected to be predominantly an N-type calcium channel current.

FIG. 9, traces B-D, shows the effect on the calcium current after exposure of the cells to increasing concentrations of GVIA. Exposure of the cells to 10 nM GVIA reduced the measured calcium current to about −857 pA. With increasing concentrations of OCT peptide, the measured calcium current dropped to −534 pA, at 50 nM OCT peptide, and to −257 pA, at 200 nM OCT. The peptide concentration at which 50% inhibition of calcium current is produced is determined from the voltage-gated current amplitudes, plotted as a function of OCT peptide concentration.

The calculated $ED_{50}$ is 12 nM for GVIA and 115 nM for MVIIA, indicative of high inhibitory peptide activity. The $ED_{50}$ concentration for test OCT peptides can be readily determined in a like manner. Test peptides which have $ED_{50}$ values of less than about 1 μM in the above neuroblastoma system are classed as having the requisite calcium current inhibitory activity. More generally, test peptides whose $ED_{50}$ values for calcium current inhibition is within the range of that for OCT peptides MVIIA MVIIB, GVIA, GVIIA, and RVIA are selected for their potential as neuroprotective agents.

Test peptides which are inhibitory for neuronal cell calcium currents can be further tested in non-neuronal cells, to confirm that the peptide activity in blocking calcium currents is specific to neuronal cells. A variety of muscle cell types which are refractory to calcium-current inhibition by OCTs, such as vertebrate embryo heart and skeletal muscle cells, are suitable. Cell current measurements are made substantially as outline above and detailed in Example 7.

Figure 10:
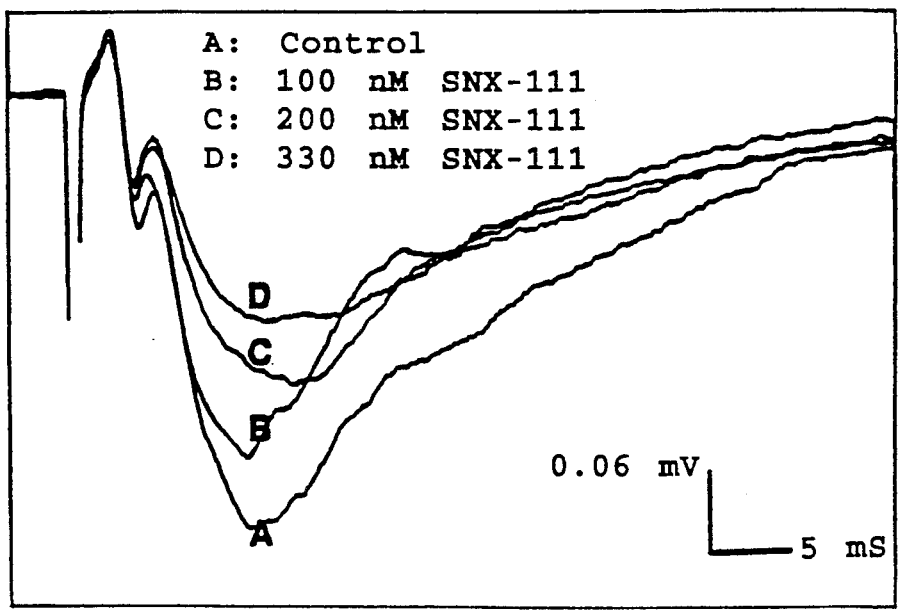
FIG. 10 shows plots of EPSP in an untreated hippocampal slice (trace A), and in hippocampal slices exposed to increasing concentrations of OCT peptide MVIIA (SNX-111) (traces B-D)

One suitable system for measuring function of central presynaptic voltage-sensitive calcium channels is the rat hippocampal slice, as detailed in Example 7B. A constant-current pulse (typically 200 μsec in length) is applied using a stimulating electrode to elicit neuronal activity. Stimulation is typically applied to the striatum radiatum, and consequent voltage events are recorded using a separate extracellular recording electrode placed a few millimeters away. Evoked activity in the dendritic portion of the neurons is recorded with an electrode in the striatum radiatum, while evoked activity in the cell bodies or neurons is recorded with an electrode in the striatum pyramidale. The extracellular recordings shown in FIG. 10A illustrate the excitatory post-synaptic potential (EPSP) in the dendritic region which is recorded in the absence of added drug or compound. This EPSP is a summation of a series of cells firing in response to the stimulating pulse and hence represents electrically the release of neurotransmitter from a presynaptic terminal and its electrical effect on a post-synaptic neuron. FIG. 10 (B-D) shows that in the presence of increasing concentrations of MVIIA (SNX-111), the magnitude of the EPSP is reduced. Such a reduction of EPSP can be due to either pre- or post-synaptic events. In this case, it is thought to be due to blockade of the presynaptic voltage-gated calcium channel. Blockade of this channel results in decreased release of neurotransmitter into the synapse.

As noted above, high affinity OCT peptides are also inhibitors of neurotransmitter release in selectively neuronal cell, as evidenced by inhibition of neurotransmitter release in neuronal cells, but not at a mammalian neuromuscular junction of a skeletal muscle.

One standard assay method for measuring neurotransmitter release is based on measured ATP release from synaptosomes, such as electric organ synaptosomes, as detailed in Example 8A. Test peptides are included in the synaptosome medium at concentration of between about 1 to 1000 nM, and the reduction in ATP levels is measured before and after peptide addition. From a plot of ATP release inhibition as a function of peptide Concentration, the $IC_{50}$ value, at which 50% ATP release inhibition occurs, is determined. The measured $IC_{50}$ values determined for the MVIIA an GVIA peptides are 10 nM and 130 nM, respectively.

Another test method for inhibition of neurotransmitter release, detailed in Example 8B, is based on inhibition norepinephrine from mammalian hippocampal slices. FIG. 8 show basal (open bars) and stimulated (solid bars) levels of norepinephrine in rat hippocampal cells, and the inhibition of stimulated levels at increasing MVIIA. From this data, the MVIIA concentration effective to reduce stimulated level above basal level by 50% ($EC_{50}$) is determined to be 5 nM. Table 5 below shows $IC_{50}$ values for two high affinity OCT peptides, MVIIA and GVIA, one low-affinity peptide, SVIA, and test compound TVIA. As seen, TVIA is within the $IC_{50}$ range of high affinity OCT peptides, and clearly distinguishable (50 fold activity difference) from low-affinity OCT SVIA. More generally, the test compound is selected for antagonist activity if its $IC_{50}$ level for inhibition of neurotransmitter release is within the range of values seen for high-affinity OCT peptides MVIIA, MVIIB, GVIA, GVIIA, and RVIA.

TABLE 5

| Compound | $IC_{50}$ |
|---|---|
| GVIA | <1 nM |
| MVIIA | 4 nM |
| TVIA | 12 nM |
| SVIB | 300 nM |

Compounds which can be classed as both high-affinity binding and inhibitory compounds, by the screening methods of the invention, may be further screened for in vivo activity in a mouse shaker model system. It was earlier reported that intracerebroventricular (ICV) administration of MVIIA peptide in mice produces whole-body tremors (Olivera). Subsequently it was discovered in studies conducted in support of the above co-owned patent application that OCT peptides which were shown to have neuroprotective activity, in reducing ischemia-related damage, also gave a strong positive shaker response in mice.

In the shaker test, unanesthetized animals are given a selected dose of the test compound by ICV administration. Animals which show spontaneous tremors within about 30 minutes after compound administration are scored as positives. Table 7 in Example 9 shows the shaker results obtained on tests with in creasing doses of OCT's MVIIA, GVIA, and SVIA. The middle column shows the number of animals which were tested at each dose, and the right column, the percent of "shakers", i.e., animals showing shaking behavior. The MVIIA and GVIA OCT peptides, which are both active as judged by the binding and inhibition criteria described above, give a dose-dependent shaker response, with both peptides showing a high percentage of shakers at 0.3 µg dose. By contrast, the SVIA peptide, which is inactive by the above binding activity criterion, gives only a low percentage of shakers, even at a dose of 10 µg.

From the foregoing, it can be appreciated how the screening method of the invention facilitates the screening of effective neuroprotective compounds. One criterion for an effective neuroprotective compound, for use in reducing neuronal damage in ischemia-related injury, is the ability to inhibit the spread of neuronal damage from the site of injury. Evidence indicates that the spread of damage in ischemia-related injury is due, at least in part, to release of transmitter(s) from damaged cells, triggering calcium influx into adjacent cells, with consequent spread of cellular injury and release of neurotransmitter from injured cells. In the screening method of the invention, compounds are selected for binding to OCT binding sites at which high-affinity binding correlate with marked inhibition of calcium channel activity and neurotransmitter release.

A second criterion for an effective neuroprotective agent is a selective effect on neuronal cells. According to an important aspect of the present invention, OCT binding sites on neuronal membranes appear to be specific for neuronal cells, as evidenced by the ability of high-affinity OCT peptides to inhibit calcium channel currents and neurotransmitter release selectively in neuronal cells, but not in muscle cells. Compounds selected by the screening method of the invention are thus predicted to be neuronal-cell specific.

Based on the screening for high-affinity binding alone, three compounds were identified. One of the compounds, TVIA, was further screened for activity as an inhibitor of calcium currents/neurotransmitter, for activity in the mouse shaker test, and was identified as having an activity in these tests which is within the range of high-affinity OCT compounds.

IV. Treatment Method

In another aspect, the present invention provides a treatment method for reducing neuronal damage related to an ischemic condition in a human patient, by administration of a pharmaceutically effective amount of a compound selected in accordance with the screening method just described.

The ischemic conditions may be due to an interruption in cerebral circulation, such as caused by cardiac failure, or other condition leading to global loss of blood supply to the brain, or to localized interruptions in blood flood, such as due to cerebral hemorrhaging, or localized thrombotic or embolic events, or head trauma.

The ischemic condition to be treated is generally associated with stroke, defined as the sudden diminution or loss of neurological function caused by an obstruction or rupture of blood vessels in the brain. In stroke, as well as in other types of cerebral ischemic conditions, the treatment is aimed at preventing or reducing secondary brain damage resulting from the original ischemic event. The secondary damage typically includes cerebral cell destruction, or lesions, in the area surrounding the ischemic injury, in the case of focal ischemia, and also in areas of selective vulnerability in lesions, such as the hippocampus or basal ganglia, in the case of global ischemia. The secondary damage may often be manifested by functional impairment, such as loss of short-term or long-term memory. As will be seen below, treatment by compounds having the desired binding and inhibitory activities is effective in reducing or preventing both anatomical and functional secondary damage related to ischemia.

The compound administered in the present invention includes any compound identified by the method described in Section II, including new OCT peptides and peptide analogs, OCT peptide fragments, and non-peptide compounds which mimic the binding activity of a high-affinity OCT peptide for OCT-binding sites on neuronal membranes.

The compound is formulated for parenteral administration in a suitable inert carrier, such as a sterile physiological saline solution. The concentration of peptide in the carrier solution is typically between about 0.1–10 mg/ml. The dose administered will be determined by route of administration. One suitable route is intracerebroventricular (ICV), at a dose level of about 0.1–50 µg compound/kg body weight, depending on the binding and inhibitory values of the compound. A pharmaceutically effective dose, i.e., a dose effective to produce significant reduction in anatomical and/or functional damage, can be estimated, as noted above, from the dose response seen in the mouse shaker model. The dose level can also be estimated by comparison with established effective doses for known OCT peptides, corrected for observed differences in in vitro binding and inhibitory activity.

As reported below, it has been found that there is little or no loss of protective effect of the compound when administered well after the ischemic effect, e.g., one hour following the period of transient occlusion. The delayed-administration protective effect indicates that the compound is effective in blocking the events leading from ischemic injury to secondary cerebral injury, since these events may occur over a period of many hours or even days after injury. Thus, the delayed administration may be effective to reduce secondary cerebral damage over a several hour period, or even a day or more, following the onset of ischemia.

The treatment method has been demonstrated in two animal systems which are widely employed as model systems for global ischemia and secondary stroke damage. The first system is the gerbil model of global ischemia produced by transient occlusion of carotid arteries of the neck. For clinical comparisons, the ischemia produced in this model has been likened to that produced by cardiac arrest, since all blood flow to the brain is stopped for a fixed period, typically 5–10 minutes.

Although some differences in particular sequelae have been noted between species, gerbils exhibit the same kind of selective regional damage to ischemia as is found in other mammals, including humans. In particular, the characteristic secondary damage observed in the hippocampal CA1 region is similar to that seen in other mammals, including humans (Kirino; Yamaguchi). Neurons in this area, and especially pyramidal neurons, exhibit a delayed neuronal death over a period of up to 4 days after ischemic injury.

The second model is the rat four-vessel occlusion model The experimental procedure for producing temporary occlusion produces an ischemia that mimics conditions in the human brain following cardiac arrest, including the following similarities the ischemic event is temporary, typically 5-30 minutes; it occurs in an unanesthetized state; in most rats, the ischemic event is not accompanied by generalized seizures, and animals that have seizures can be excluded from the study. In addition the occlusion procedure allows the animals to be easily monitored, maintained and analyzed.

A. Reduction in Anatomical Damage

Ischemia in the gerbil model system was induced in anesthetized animals by occluding the two carotid arteries for eight minutes, as detailed in Example 10. OCT peptide was administered ICV during the occlusion period, or one hour following occlusion. Four days after occlusion and peptide treatment, the animals were examined histologically for anatomical damage in the hippocampal CA1 region, as detailed in Example 10.

Figure 12A:
FIGS. 12A and 12B are low-power micrographs of gerbil hippocampus CA1 region in animals after ischemia, and infusion of MVIIA OCT (12A) or drug vehicle (12B)
Figure 12B:
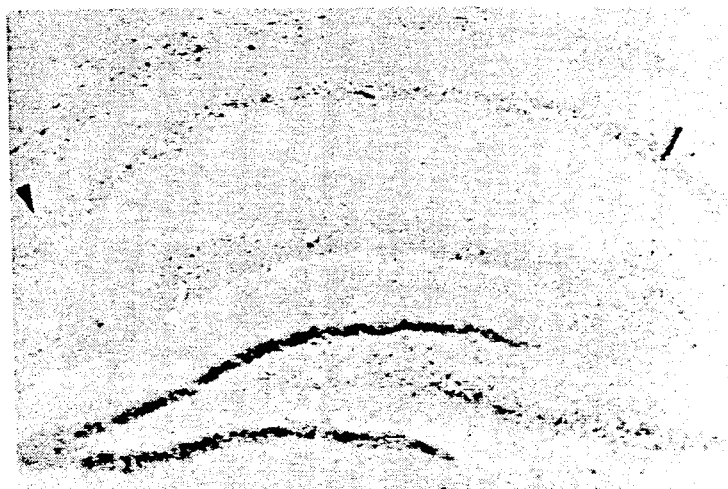
Figure 13A:
FIGS. 13A-13D are higher power micrographs of cells in the drug-treated ischemic animals (13A), in animals receiving vehicle alone (13B), in animals showing complete protection by OCT against ischemic cell damage (13C); and in animals showing partial protection by OCT against ischemic cell damage (13D)
Figure 13B:
Figure 13C:
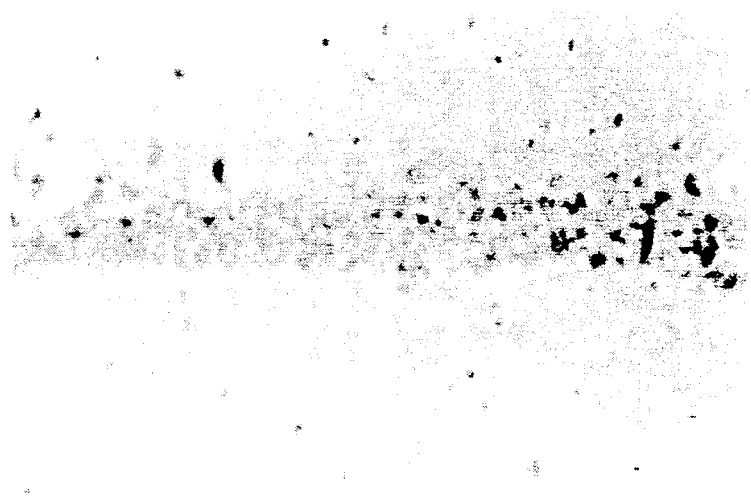
Figure 13D:
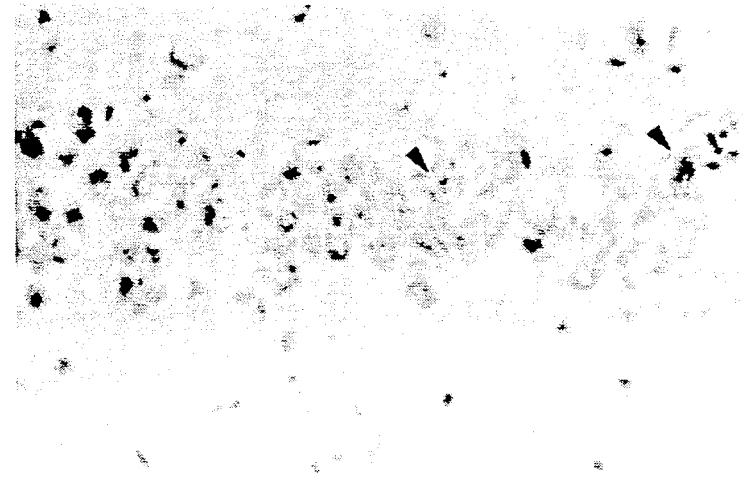

FIGS. 12A and 12B are low-power micrographs of gerbil hippocampus CA1 region in animals after ischemia, and infusion of MVIIA OCT (12A) or drug vehicle (12B). The arrows in the figures indicate the approximate borders of the CA1 region. At higher power, cells in the drug-treated ischemic animals appear normal (FIG. 13A), whereas damage is apparent in the ischemic animals receiving vehicle alone (FIG. 13B). Another example of complete drug protection is seen in FIG. 13C, and an example of partial protection is seen in FIG. 13D, where there are a small number of damaged cells.

Anatomical sections, such as those seen in FIGS. 12 and 13, were scored according to the criteria set out in Example 11. The extent of anatomical damage in ischemic animals treated with MVIIA or GVIA OCT or receiving vehicle alone (control), based on the above scoring system, is given in Table 10 in Example 11B. The peptide was administered by ICV infusion during the eight minutes of ischemia, at a total dose indicated in the table below. As seen, the extent of damage in the higher-dose MVII OCT treated animal was only 25% of that in untreated animals. The GVIA peptide also produced more than a 50% reduction in damage, and the lower dose was near maximal effectiveness.

Ischemia in the rat model system was induced by first surgically closing the vertebral arteries, and after surgical recovery, transiently blocking the carotid arteries (thus completely blocking blood flow to the brain) for a period of 15 minutes. During occlusion, animals were given 0.3 μg OCT MVIIA peptide ICV. Four days after occlusion, the animals were examined histologically, as above, to determine the extent of damage in the hippocampal CA1 region, as above. The mean scores are given in Table 12 in Example 11C. As seen, the extent of damage in the treated animals was only about ⅓ that in untreated animals.

B. Functional Activity Protection: Hyperactivity

One common consequence of cerebral ischemia in animals is hyperactivity, which can be seen as pacing (exploratory) behavior within a few hours of occlusion, and can be observed up to several days later. Hyperactivity in ischemic gerbils, was monitored as described in Example 12. Briefly, gerbils were tested individually for 60 min, with cumulative activity counts recorded every 15 min for statistical analysis. Baseline activity was measured before surgery to ensure comparability of the different treatment groups on this measure, and activity measurements were made at 1 and 3 days after occlusion.

B. Functional Activity Protection: Spontaneous Alternation

Damage to the hippocampal region of the brain is known to produce deficits in spatial learning and memory, and therefore it could be expected that ischemic damage to hippocampal cells, as documented above, might also be accompanied by loss of functional activity related to short-term memory.

One test which has been widely applied as a measure of short-term memory in experimental animals is the Y maze, in which animals are placed in the base of the stem of a Y "maze", and allowed to enter either of the two Y arms. When the animal enters an arm, a door is shut behind it. After 5 sec, the gerbil is returned to its home cage for an intertrial interval (ITI) of 2 to 12 min. At the end of that interval the animal is run in the maze again in the same way. Most normal animals will alternate, that is, will enter the arm that was not entered on the first trial. The test is scored by a "Y" for alternation and an "N" for repeat selection of the same Y arm.

In the test procedure, ischemia in gerbils was induced as above, with simultaneous ICV administration of vehicle (control) or 0.1 or 0.3 μg OCT MVIIA or GVIA peptide (results from all drug treatments were combined, as described in Example 11). Three days after occlusion, the animals were tested in the Y maze. Results of the spontaneous alternation tests are summarized in Table 13 of the example for animals for which there was anatomical protection from doses of at least 0.1 μg of either compound.

As seen from the data in the table, the normal Y/N ratio for control animals (no occlusion, ICV administration of vehicle) was about 2:1. Ischemic injury produced a drop in this ratio to less than 1, indicating substantially random behavior in the Y test. The loss of short-term memory seen in ischemic animals was completely prevented by peptide treatment, with Y/N ratios of about 2:1 being obtained. Peptide alone in the absence of ischemic injury appeared to enhance the Y/N ratio, and this enhancement may contribute to the improved performance of treated, ischemic animals.

The foregoing demonstrate the effectiveness of OCT compounds characterized by (a) high binding affinity to OCT binding sites in neuronal tissue and (b) selective inhibition of calcium channel currents and neurotransmitter release in reducing neuronal damage in ischemia-related injury. Based on the apparent mechanism of action of the OCT peptides, it can be predicted that screened compounds which show the same selective binding and inhibitory properties would be similarly effective as neuroprotective agents.

The following examples are intended to illustrate methods for preparing OCT peptides, test methods for determining in vitro and in vivo binding and inhibitory activities, and exemplary treatment results. The examples are in no way intended to limit the scope of the invention.

EXAMPLE 1

Preparation of OCT Peptides

Abbreviations used in this example are BOC, tertiary butoxycarbonyl; DCM [see notes regarding this Example, pg. 34], dichloromethane; TFA, trifluoroacetic acid; IPM, N-isopropylmorpholine; BOC-AA-OH, BOC amino acid; DIEA, diisopropylethylamine; 2-ClZ, chlorobenzyloxycarbonyl; tosyl, p-toluenesulfonyl; DMF, N,N-dimethylformamide; TFE, trifluoroethanol; SA, symmetrical anhydride of BOC-AA-OH; DCCI, N,N-dicyclohexylcarbodiimide; D, dichloromethane; E, ethyl ether; P, petroleum ether.

Commercially available benzhydrylamine-resin hydrochloride, Lot No. B30101, was obtained from Beckman Instruments Inc., Palo Alto, Calif. With this resin, cleavage of a peptide formed on the resin, under the conditions described below, produces a peptide which is amidated at its carboxy end.

A. Preparing Protected Amino Acid Anhydrid

Each BOC-AA-OH (2.4 mmol) was dissolved in 5 ml $CH_2Cl_2$ and cooled to 0° C. The volume of DCM used for BOC-Leu-OH (dried in vacuo) was 12 ml, and the BOC-Leu-OH solution was not cooled. 2 ml 0.6M DCCI in DCM was added and the mixture stirred at 0° C. for 15 min. For BOC-Leu-OH, the mixture was also cooled after this addition. Precipitation of N,N-dicyclohexylurea was completed by storage at −20° C. for 1.5 hour, after which the precipitate was filtered and washed with ethyl ether (5 ml). The filtrate was evaporated to remove solvents and the product was crystallized in the solvent system given in Table 6. Residual amounts of DCM can affect the exact conditions for crystallization. Recrystallization was performed by dissolving in DCM, evaporating most of the solvent, and recrystallizing from the appropriate solvent.

TABLE 6

| Amino Acid | Solvent |
|---|---|
| Ala | DCM |
| Asp (Benzyl) | E:P |
| Cys (4-MeBenzyl) | DCM |
| Gly | E:P |
| Leu | P |
| Lys (2-ClZ) | E:P |
| Met | E:P |
| Ser (Benzyl) | E:P |
| Thr (Benzyl) | E:P |
| Tyr (2-BrZ) | DCM |

B. Preparation Of MVIIA

Synthesis of MVIIA peptide was performed in a Beckman Model 990 Peptide Synthesizer by a solid-phase method based on the primary structure shown in FIG. 1A.

A double coupling protocol was used for the incorporation or residues Cys-25 through Tyr-13, and a triple coupling protocol for amino acids Met-12 through Cys-1. Symmetrical anhydrides were used in crystalline form as described in Yamashiro. Crystalline symmetrical anhydrides (1.0 mmole) were each dissolved in 6 ml DCM and stored in the amino acid reservoirs at 4° C. Sidechain protecting groups used were: Cys, 4-MeBenzyl; Lys, 2-ClZ Ser, Benzyl; Arg, Tosyl; Thr, Benzyl; Asp, Benzyl; Tyr, 2-Br-Benzyl.

Unless specified, volumes were 8 ml, except for step 2 below, which was 10 ml, and all reactions were carried out at room temperature. After incorporation of the Asp-14 residue, the volume of step 2 was increased to 15 ml while all other volumes were raised to 10 ml after incorporation of the Arg-10 residue The double coupling protocol consisted of steps 1–16 listed in Table 2 below.

Amino acids Met-12 through Cys-1 were added by a triple coupling protocol which included, in addition to steps 1–16, steps 17–19 in Table 7.

TABLE 7

| Step | Reagent |
|---|---|
| 1 | DMC wash (3 times) |
| 2 | 67% TFA/M (20 min.) |
| 3 | DMC wash (2 times) |
| 4 | 25% dioxane/DMC wash (2 times) |
| 5 | 5% DIEA/DMC wash |
| 6 | DMC wash |
| 7 | 5% DIEA/DMC wash |
| 8 | DMC wash (5 times) |
| 9 | 1.0 mmol SA in DMC (5 min) |
| 10 | 0.5 mmol IPM in 3 ml TFE plus 1 ml DMC (5 min) |
| 11 | 0.5 mmol IPM in 5 ml DMC (5 min) |
| 12 | DMF wash (3 times) |
| 13 | 1.0 mmol SA in DMF (5 min) |
| 14 | 0.5 mmol IPM in 5 ml DCM (5 min) |
| 15 | 0.5 mmol IPM in 4 ml DMF (5 min) |
| 16 | DMC wash |
| 17 | DMC wash (2 times) |
| 18 | 1.0 mmol SA in DCM (5 min) |
| 19 | 0.5 mmol IPM in 4 ml DMF (5 min) |

Crystalline symmetrical anhydrides (1 mmole) were each dissolved in 6 ml DCM or DMF and stored in the amino acid reservoirs at 4° C. Side-chain protecting groups used were: Cys, 4-MeBzl; Lys; ClZ; Ser, Bzl; Arg, tosyl; Thr, Bzl; Asp, Bzl; Tyr, BrZ.

For BOC-Arg(tosyl)-OH, the following mixture was prepared: 1.87 BOC-Arg(tosyl)-OH, 0.57 g 1-hydroxybenzotriazole, 15 ml DMF, stirred to dissolve, cooled to 4° C., added 0.52 ml diisopropylcarbodiimide, and split in half for steps 9 and 13. For this coupling, the protocol was modified as follows: step 8 was 3 times DCM wash and 2 times DMF wash; step 9 was for 10 min; step 11 was for 10 min; step 13 was for 10 min; step 14 was 0.4 mmol IPM in 4 ml DMF for 10 min; step 15 was for 10 min; step 16 was 1 times DMF wash and 1 time DCM wash. Reaction mixtures in steps 9, 10, 13, 14 and 18 were not drained.

The mixture for a third coupling for incorporating the Arg-10 residue consisted of 1.00 g BOC-Arg(tosyl)-OH, 1 ml DMF, 5 ml DCM, stirred to dissolve, and cooled to 4° C. to which is then added 1.67 ml 0.6M DCCI in DCM.

After the last amino acid had been incorporated, the protected peptide resin was subjected to steps 1–4 to remove the N-terminal BOC group, collected on a filter with use of ethanol, and dried in vacuum to yield 2.61 g.

C. Deblocking and cleavage in liquid HF.

A mixture of protected peptide resin (1.32 g), 2-mercaptopyridine (0.50 g), p-cresol (2.6 g), and liquid hydrogen fluoride (HF) (25 ml) was stirred at 0° C. for 80 min. The liquid HF was evaporated with a rapid stream of nitrogen gas, first below 0° C. then at 24° C. The mixture was stirred in ethyl acetate (25 ml) until a finely divided solid was obtained. The solid was filtered, washed with ethyl acetate, and air dried to yield 1.09 g. This solid was stirred in 50% aqueous acetic acid (10 ml) to dissolve the peptide material, filtered, and washed with 20 ml water. The filtrate was freeze-dried to yield 450 mg of fluffy powder.

D. Formation of disulfide bridges

A sample (300 mg) of the fluffy powder was dissolved in 30 ml of 0.05M ammonium bicarbonate, 10 mM dithiothreitol (DTT), and 2M guanidine hydrochloride. The solution, which had a pH of 6.7, was allowed to stand at 24° C. for 2 hr, then diluted with 120 ml of water and stirred for 20 hr at 24° C. DTT (25 mg) was added and the solution allowed to stand at 24° C. for 80 min. The mixture was then stirred at 4° C. for 3 days.

E. Isolation of MVIIA OCT

The solution from Part D was acidified with glacial acetic acid (2 ml), evaporated in vacuo to a low volume, and fractionated by gel filtration on Sephadex G-25 in a 2.5 x 48 cm column, using N acetic acid, to remove peptide polymeric species (exclusion volume), and salts (slowest moving peak). Fractions (5 ml) were collected, with peptide absorbance monitored at 280 nm. Fractions corresponding to the monomer peptide were pooled and freeze-dried to give 127 mg of fluffy powder. A sample of the monomeric material (34 mg) was purified by preparative HPLC on a Vydac 218TP1022 column with a gradient of 10–20% acetonitrile in 0.1% trifluoroacetic acid over 50 min at 8 ml/min, with detection at 226 nm and collection of 4 ml fractions. Fractions corresponding to the major peak were pooled, evaporated in vacuo to remove acetonitrile, and freeze-dried to yield 7.7 mg. Analytical HPLC on a Vydac 218TP104 column with the same solvent and gradient over 10 min followed by 10 min of isocratic elution at the 20% composition (1.5 ml/min) gave a single peak identical in behavior to an authentic sample of OCT MVIIA. Amino acid analysis of a 24-hr HCl-hydrolysate gave: Asp, 0.93; Thr, 1.05; Ser, 2.85; half-cystine, 5.2; Gly, 4.08; Ala, 1.07; Met 0.94; Leu, 1.02; Tyr, 0.85; Lys, 3.98; Arg, 2.09.

F. Radio-Iodination of MVIIA

MVIIA peptide was iodinated by reaction with Iodogen TM in the presence of NaI according to Cruz et al., with minor modification. 2 m Ci of carrier-free Na$^{125}$I, 75 ul 0.5M phosphate buffer pH 7.4 and 20 ul of 1 ug/ul peptide were added to a polypropylene test tube coated with 10 ug Iodogen TM. The tube was agitated for 8 minutes, and the solution was chromatographed by HPLC through a 10×0.46 cm C-8 reverse phase column with a pore size of 300 Å (Brownlee Labs, Santa Clara, Calif.). The sample material was eluted with a gradient from 0.1% trifluoroacetic acid to 60% acetonitrile in 0.1% trifluoroacetic acid. The major peak of active radio-iodinated peptide was resolved at about 2 minutes greater retention time than the underivatized peptide.

The fractions containing this peak were collected and later diluted for use in binding experiments. MVIIA, iodinated under the conditions as above except with non-radioactive NaI, was tested for the ability to inhibit depolarization-dependent ATP release from synaptosomes as described in Ahmad, S. N. and Miljanich, G. P. (1988) Brain Research 453:247-256 and found to be as potent in this regard as the underivatized peptide.

G. Synthesis of Other OCT Peptides

Synthesis of each of the OCT peptides shown in FIGS. 1B-1H was according to the solid-phase method described in Example 1, except that a single coupling protocol involving steps 1-12 in Example 1, Part C was used for coupling the first 10 C-terminal amino acids residues, and a double coupling method involving steps 1-16 in Example 1, Part C was used for coupling the final n−10 N-terminal residues, where n is 24-29. Releasing the peptide from the solid support, removing the blocking groups, and joining the disulfide bridges were carried out substantially as above. The peptide was separated from salts and polymeric peptide species by gel filtration on Sephadex G-25, and purified on preparative HPLC as described in Example 1. For binding studies, each peptide can be radioiodinated essentially as above.

EXAMPLE 2

Preparation of OCT Peptide Fragments

Synthesis of each of the OCT peptide fragments shown in FIGS. 2A-2L and 3A-3B was performed according to the solid-phase method described in Example 1, except that a single coupling protocol involving steps 1-12 in Example 1, Part C was used for coupling all of the residues in each fragment.

Releasing the peptide fragment from the solid support, removing the blocking groups, and joining the disulfide bridges were carried out substantially as above. The peptide fragments were purified on preparative HPLC as described in Example 1, Part E.

EXAMPLE 3

Synaptosome Preparations

A. Fish Synaptosomes

Electric organ synaptosomes were prepared by dissection from marine electric rays (*Ommata dyscopyge* or *Narcine brasiliensis*) that had been stunned with 0.25 g/liter tricaine HCl and cooled to 4° C. immediately prior to dissection. All subsequent manipulations were carried out at 0°-4° C. whenever possible. Organs were diced and homogenized for 4 15-second periods in a Waring blender with an equal weight of synaptosome buffer (SB) (20 mM HEPES, Ph 7.2, 280 mM NaCl, 3mM KCl, 1.8 mM MgCl$_2$, 300 mM urea, 100 mM sucrose, 5.5 mM glucose plus protease inhibitors), (1 mM EGTA, 1 μM pepstatin, 2 μM leupeptin, 1 μg/ml aprotinin and 0.1 mg/ml bacitracin).

The homogenate was filtered through cheesecloth and centrifuged at 30,000×g for 15 min. The supernatant was discarded and each pellet was taken up in 10 ml synaptosome buffer plus protease inhibitors. The resuspended pellets were combined and further disrupted with 5 strokes of a Teflon pestle in a glass homogenizer set at 400 rpm. The resulting suspension was centrifuged at 30,000×g for 15 min. The supernatant was discarded and the pellet resuspended in approximately 5 ml of SB with protease inhibitors using a Teflon-glass homogenizer. This homogenate was layered onto six 32 ml 3-20% Ficoll gradients in SB (no protease inhibitors) and centrifuged at 100,000×g for 1 hour in a swinging bucket rotor. The synaptosome band (the first band below the buffer-gradient interface) of each gradient was aspirated off and diluted 2:1 with synaptosome buffer with protease inhibitors. The diluted synaptosome suspension was pelleted at 30,000×g for 15 min and resuspended in synaptosome buffer and refrigerated, for use in ATP release assays within 2-3 days of preparation. For binding experiments, aliquots were frozen at −160°.

B. Mammalian-Brain Synaptosomes and Synaptosomal Membranes

Rats were anesthetized with ether prior to decapitation Forebrains were removed, weighed and transferred to 10 ml ice-cold 0.32M sucrose plus protease inhibitors (PI): 1 mM EGTA, 1 mM EDTA, 1 uM pepstatin, 2 uM leupeptin, 1 mM PMSF. Brains were homogenized using a motor-driven Teflon-glass homogenizer (approx. 8 passes at 400 rpm). Homogenates from 4 brains were pooled and centrifuged at 900×g for 10 minutes at 4 degrees. Supernatants were then centrifuged at 8,500×g for 15 minutes. Resulting pellets were resuspended in 10 ml each ice-cold 0.32M sucrose with vortex mixing. The suspension was then centrifuged at 8,500×g for 15 minutes. Pellets were resuspended in 20 ml ice-cold 0.32M sucrose plus PI. The suspension (5 ml/tube) was layered over a 4-step sucrose density gradient (7 ml each: 1.2M sucrose, 1.0M sucrose, 0.8M sucrose, 0.6M sucrose). Gradient tubes were centrifuged in a swinging bucket rotor at 150,000×g for 60 minutes at 4 degrees. The 1.0M sucrose layer plus the interface between the 1.0 and 1.2M sucrose layers were collected and diluted with ice cold deionized water plus PI to yield a final sucrose concentration of 0.32M. The resulting suspension was centrifuged at 8,500×g for 15 minutes. Pellets were then resuspended in 5 ml ice-cold Phosphate buffered saline plus PI. These resulting rat brain synaptosomes were then aliquoted and stored at −80 degrees C.

Prior to use in binding assays, synaptosomes were thawed and diluted with 3 volumes of ice cold deionized water. This suspension was homogenized using a PT 10-35 Polytron (setting 6) for two 10-second bursts. The homogenate was centrifuged at 40,000×g for 20 minutes at 4 degrees. The resulting pellets were resuspended in about 5 ml of ice cold phosphate buffered saline plus PI plus sodium azide (0.002%). The resulting brain synaptosomal membrane preparation could be stored at −80 degrees.

EXAMPLE 4

OCT Peptide Binding to Synaptosomal Membranes

A. Fish Synaptosomes

The OCT peptides whose synthesis is described in Example 2 were tested for binding to elasmobranch electric organ synaptosomes (also referred to herein as fish synaptosomes), using a competitive binding assay based on displacement of radiolabeled OCT MVIIA by the test peptide or peptide fragment. Total binding was measured using $^{125}$I-MVIIA OCT alone, and non-specific binding was determined by measuring $^{125}$I-MVIIA OCT bound in the presence of 1 uM unlabeled MVIIA OCT. The difference between these values represents $^{125}$I-MVIIA OCT specifically bound to OCT binding sites.

The binding constant (K°) for MVIIA OCT to fish synaptosomes was determined by a saturation binding method in which increasing quantities of the OCT were added to aliquots of a synaptosome preparation. The amount of labeled peptide specifically bound at each concentration was used to determine $B_{max}$, the concentration of specific binding sites on the synaptosomes, and $K_d$, following standard binding analysis methods (Bennett, J. P., and Yamamura, H. I., Neurotransmitter Receptor Binding, pp. 61–89, Raven Press, N.Y. (1983).

In the competitive displacement binding assays, binding was initiated by adding a quantity of synaptosomal membranes (10 ug protein) suspended in 400 ul binding medium (20 mM HEPES, pH 7.4, 125 mM NaCl, 0.1 mM EDTA, 0.1 mM EGTA, 1 mM PMSF, 2 uM leupeptin, 1 uM pepstatin, and 125 mM NaCl in 20 mM HEPES (pH 7.4) and 0.1% gelatin) to a series of tubes $^{125}$I-MVIIA and test substances ranging in concentration from approximately $10^{-4}$M to $10^{13}$M. An additional tube containing 1 uM unlabeled MVIIA OCT was included to measure nonspecific MVIIA binding. Final assay volume was 500 μl. Assay tubes were incubated for 100 minutes at 4° C. on a rotating mixer. Concentration of [$^{125}$I]MVIIA OCT varied from assay to assay, and ranged from 50–275 pM.

Separation of bound $^{125}$I-MVIIA OCT from unbound peptide was achieved by rapid vacuum filtration of 150 ul aliquots of binding mixture from each tube through Whatman GF/C glass-fiber filters presoaked in an aqueous 0.6% polyethyleneimine. Tissue-bound $^{125}$I-MVIIA OCT retained on the filters was washed three times with 3.5 ml of ice-cold wash buffer consisting of 20 mM HEPES (pH 7.4), 125 mM NaCl, and 0.1% gelatin. Filters were dried and bound radioactivity was measured in an LKB gamma counter at 75% counting efficiency.

The binding constant $K_i$ for each test substance was calculated using non-linear, least-squares regression analysis (Bennett & Yamamura) of competitive binding data from 2 assays performed in duplicate on separate occasions. The relationship between Ki and IC$_{50}$ (concentration at which 50% of labeled compound is displaced by test compound) is expressed by the Cheng-Prusoff equation:

$$Ki = \frac{IC_{50}}{I} + \frac{[L]}{Kd}$$

where IC$_{50}$ is the concentration of test substance required to reduce specific binding of labeled ligand by 50%; [L] is the concentration of [$^{125}$I]MVIIA OCT used in the experiment; and $K_d$ is the binding constant (680 pM) determined for binding of [$^{125}$I]MVII OCT to fish synaptosomal membranes in saturation binding experiments.

B. Results

Representative displacement binding curves for fish synaptosomes (EOS) are illustrated in FIG. 3. Bound $^{125}$I-MVIIA OCT is expressed as % control for direct comparison of individual experiments. In the experiments, compounds which displace $^{125}$I-MVIIA OCT at lower concentrations have higher relative affinities for the omega-conopeptide binding site. Thus, MVIIA has the highest affinity and SVIA has no observable affinity for the w-conopeptide binding site as measured by $^{125}$I-MVIIA OCT binding in the experiments shown. Table 1 summarizes computed Ki values for various OCT peptides for fish synaptosomes.

Mammalian Synaptosomes

Binding of [$^{125}$I]MVIIA OCT to rat brain synaptosomal preparations was carried out under two sets of conditions. Under the first condition, the competitive binding assay was performed substantially as described in Example 4A, for MVIIA OCT. Computer-fit competitive binding curves for 2 assays performed in duplicate on separate occasions are shown in FIG. 4.

IC$_{50}$ values were computed from line fit curves generated by a 4-parameter logistic function. These values represent the concentration of test compound required to inhibit by 50% the total specific binding of [$^{125}$I]M-VII-OCT to rat brain synaptosomal membranes, where specific binding is defined as the difference between binding of [$^{125}$I]MVIIA OCT in the absence and presence of excess (1 μM) unlabelled [$^{125}$I]MVIIA OCT. Such values serve as approximations of the relative affinities of a series of compounds for a specific binding site.

The IC$_{50}$ values for displacement of [$^{125}$I]MVIIA OCT peptide from the series of experiments illustrated in FIG. 4 are summarized in Table 2 under the heading "Rat Brain 1."

A separate series of experiments was carried out to test OCT peptide displacement of [$^{125}$I]MVIIA OCT binding under a different set of conditions ("Rat Brain 2," Table 2). In these studies, rat brain synaptosomal membranes prepared as described in Example 3B were suspended in a binding buffer consisting of 20 mM HEPES pH 7.0, 75 mM NaCl, 0.1 mM EGTA, 0.1 mM EDTA, 2 μM leupeptin, 0.035 μg/ml aprotinin, and 0.1% bovine serum albumen (BSA). The membrane suspension was diluted and aliquoted such that each assay tube contained 10 μg membrane protein. [$^{125}$I]MVIIA OCT (25–30,000 cpm, approximately 1500–2000 Ci/mmol) and test compound were incubated with the membrane suspension in a total volume of 0.5 ml at room temperature, with shaking. After 45 minutes, assay tubes were placed in an ice bath, then filtered through GF/C filters (Whatman), prewashed with wash buffer (50 mM HEPES, pH 7.2, 125 mM NaCl, 0.1% BSA) using a Millipore filtration system. Just prior to filtration, each assay tube received 3 ml ice-cold wash buffer. The filtered membranes were washed with two 3-ml volumes of ice-cold wash buffer, dried, and filterbound radioactivity was measured in an LKB gamma counter (75% counting efficiency). (IC$_{50}$ values were calculated as described above, and are summarized in Table 2.)

EXAMPLE 5

Identification of OCT Binding Protein

Electric organ synaptosomes (EOS) were prepared as described in Example 3A. Synaptosomal membranes from rat brain hippocampal region (RHM) were prepared as described in Example 3B. An aliquot of synaptosomal preparation containing 40 μg protein was diluted in cross-link binding buffer (EOS: 25 mM PIPES, pH 6.1, 75 mM NaCl, 0.5 mM EDTA, 0.5 mM EGTA, 0.002 mM leupeptin, 0.001 mM pepstatin, 0.1 TIU/ml aprotinin, 1 mM iodoacetamide, 0.1 mM PMSF, 10% (w/v) glycerol; RHS: 20 mM HEPES, pH 7.1, 75 mM NaCl, 0.1 mM EDTA, 0.1 mM EGTA, 0.002 mM leupeptin, 0.5 TIU/ml aprotinin). This suspension was then pelleted (13,000×g, 15 min.). The pellet was then resuspended in crosslink binding buffer, pelleted again, and the resulting pellet was suspended in crosslink binding buffer to give washed synaptosomal preparations having final protein concentrations of approximately 1 mg/ml.

Binding was carried out in a total volume of 0.5 ml, containing 0.4 ml of appropriate crosslink binding buffer, 0.05 ml of washed synaptosomal preparation (concentration of binding sites: EOS, 0.5 μM; RHM, 0.05 μM), 0.05 ml of [$^{125}$I]MVIIA OCT (final concentrations: EOS: 1 nM; RHS: 0.1 nM). In separate aliquots, 0.005 ml unlabeled MVIIA OCT was added to assess nonspecific binding (EOS, 0.5 μM; RHM, 0.05 μM). Incubation was at 20°–24° for 40 min. (EOS) or 25 min. (RHM), rotating samples end over end.

Samples were then either subjected to filtration or to crosslinking, as described below. Filtration was carried out on glass fiber filters (GF/C, Whatman), using a Brandell filtration apparatus.

Crosslinking of bound [$^{125}$I]MVIIA OCT to its receptor was then carried out by adding 0.01 ml of 25 mM 1-ethyl-3-(3-dimethylaminopropyl) carbodiimide HCL (EDC) to the suspension (EDC dissolved in 25 mM PIPES, pH 6.1, immediately prior to use). The mixture was incubated for ten minutes at ice temperature, with intermittent mixing. The reaction was quenched by addition of 20 mM NH$_4$Ac. The mixture was then pelleted by centrifugation at 13,000×g for 15 min., and subsequently washed 1-2 times by resuspension in 25 mM HEPES buffer pH 7.5 and pelleting. The final pellet was dissolved in 20 μl fresh sample buffer (200 mM Tris-HCl, 10 mM DTT, 4M urea, 8% SDS, 10% glycerol, 0.1% bromphenol blue), then subjected to SDS PAGE (4-15% acrylamide gradient gel) without prior heating of the sample. Similar experiments were carried out, using [$^{125}$I]GVIA OCT as crosslink ligand FIGS. 5A and 5B show an autoradiograph demonstrating the crosslinked binding of [$^{125}$I]MVIIA OCT and [$^{125}$I]MVIIB OCT to Narcine electric organ synaptosomes (FIG. 5A) and rat brain synaptosomal (FIG. 5B) preparations. Although a number of protein bands were labeled by the procedure, binding at a protein band migrating as a 200–230 Kd protein was specifically displaced by inclusion of excess unlabelled ligand as described above.

Figure 6B:
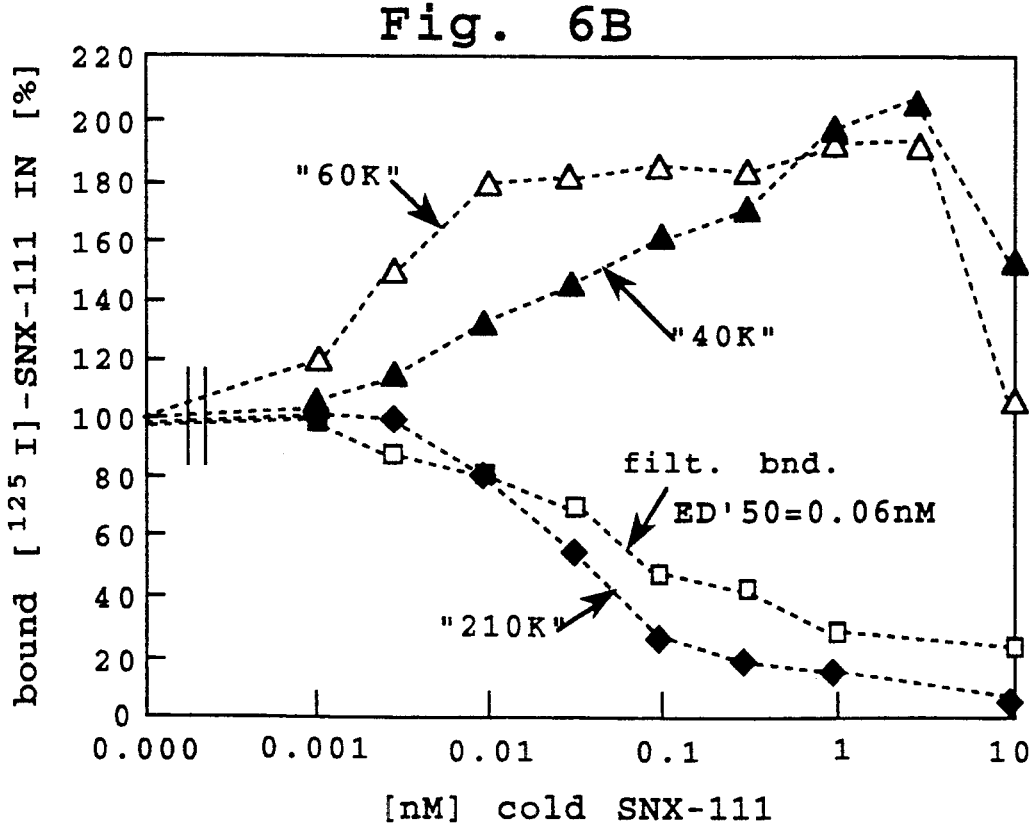

The relative specificity of displacement of crosslink OCT binding to the 200–230 Kd protein band is further illustrated in FIGS. 6A and 6B. In these experiments, [$^{125}$I]MVIIA OCT was incubated with synaptosomal membranes in the absence or presence of unlabelled MVIIA OCT, prior to crosslinking or filtration of samples, as described above. Crosslinked samples were run on SDS gels. Following autoradiography of gels to ascertain relative positions of labeled protein bands, bands were excised and radioactivity determined by gamma counting. Parallel, uncrosslinked samples were filtered, and specifically bound radioactivity was determined. In both cases, 100% bound represents that amount of radioactivity present in the absence of added unlabeled MVIIA OCT. In both EOS and RHM experiments, displacement of crosslinked [$^{125}$I]MVIIA OCT from the 200–230 Kd band parallels displacement of specific binding in the membrane filtration assay. In contrast, radiolabel was displaced from the "45K" and "654K" bands (migrating as 45 Kd and 65 Kd proteins, respectively) only at concentrations of unlabeled compound greater than about 50 nM. These results suggest that high affinity specific binding to EOS and RHM is at least in part attributable to binding at a protein band which migrates in the 200–230 Kd region on a gel. Labeling of other bands may be due to either lower affinity or non-specific binding.

Example 6

Solubilization and Partial Purification of OCT Binding Protein

A. Solubilization of OCT binding protein(s)

Electric organ synaptosomes (EOS) from *Narcine brasiliensis* containing approximately 9 mg (8.74 mg) protein were pelleted in a Beckman Airfuge for 5 minutes. Resulting pellets were pooled and resuspended in 1.68 ml solubilization buffer (50 mM HEPES, pH 7.5+20% glycerol) containing 26.2 mg digitonin (Wako; 3:1 ratio of detergent to protein), and protease inhibitors (final concentrations): leupeptin, 2uM; pepstatin A, 1 uM; EGTA, 1 mM; aprotinin, 0.1 U/ml; bacitracin, 1 mg/ml; benzamidine, 10 mM; iodoacetamide, 1 mM; phenanthroline, 1 mM; antipain, 1 uM; PMSF, 0.25 mM. The suspension was incubated for 30 minutes at 0 degrees, with mixing. The suspension was then centrifuged at 100,000 rpm for 30 minutes. The resulting supernatant contained the solubilized omega conotoxin binding protein. The presence of high affinity binding to this preparation, as evidenced by displacement of [$^{125}$I]MVIIA OCT binding is illustrated in FIG. 7, described in Part B.

B. Solubilized-Protein Binding Assay

50–100 ul of solubilized membranes were incubated for 20 minutes at room temperature with 100–250,000 cpm of [$^{125}$I]MVIIA OCT in a final volume of 0.5 ml, containing 50 mM PIPES, pH 6.25, 10% glycerol, 0.1% bovine serum albumin. Nonspecific binding was determined by inclusion of 1 uM unlabeled MVIIA OCT in duplicate tubes. Samples were filtered through 0.6% polyethyleneimine treated GF/C filters (Millipore) on a Millipore filtration unit. Protein bound [$^{125}$I]MVIIA OCT present in the PEG precipitate was determined by gamma counting. FIG. 7 illustrates displacement of [$^{125}$I]-MVIIA OCT binding by unlabeled MVIIA OCT in a digitonin solubilized preparation from Narcine EOS. The apparent affinity (Kd) of binding to this preparation of 80.8 pM (0.08 nM) suggesting a slight loss of affinity from solubilization.

C. Wheat-germ Agglutinin Affinity Chromatography

The solubilized fraction was mixed with hydrated Wheat-germ agglutinin (WGA) affinity agarose (5 mg dry weight, Vector) to form a suspension. This suspension was mixed by slow end over end rotation for 2 hours at 4 degrees. The suspension was then poured into a chromatography column, and washed with 30 ml of column buffer (50 mm HEPES, pH 7.5, 0.1% digitonin, 10% glycerol, and protease inhibitors as listed in part A, above) containing 100 mM NaCl. The column was then washed with 20 ml of column buffer. The column was eluted first with 20 ml column buffer containing 0.3M N-acetyl-D-glucosamine (NAcGln), then with 20 ml of column buffer containing 0.3M NAcGln and 100 mM NaCl. Fractions of the above wash and elution profile were assayed for binding of 125I-MVIIA OCT. Fractions found to have peak binding activity were loaded onto a MVIIA OCT affinity column, as described below.

D. Preparation of MVIIA OCT Affinity Column

Four milliliters of Affigel 10 (BioRad) were transferred to a glass fitted funnel and washed with 30 ml of ice cold isopropyl alcohol, followed by 30 ml of ice-cold deionized water. The semi-dry gel was transferred to a 15 ml conical polypropylene centrifuge tube. To the gel was added 2.5 ml of a solution containing 5 mg MVIIA OCT in 0.1M HEPES, pH 7.4, 20 mM $CaCl_2$, 6M urea. This solution was incubated for 6 hours at room temperature with mixing, then transferred to a chromatography column and washed with 200 ml of affinity column buffer (50 mM PIPES pH 6.25, 10% glycerol, 0.1% digitonin, 1 ug/ml leupeptin, 1 ug/ml aprotinin).

E. Affinity chromatography on MVIIA OCT affinity column

Pooled fractions having peak binding activity from the WGA agarose column were loaded onto an MVIIA OCT affinity column (bed volume 3.5 ml) at a flow rate of 0.375 ml/min. The flow through was reloaded onto the column a second time. The column was then washed with 35 ml affinity column buffer, then eluted with 50 mM sodium acetate, pH 5, 0.5M NaCl, 10% glycerol, 0.1% digitonin, 1 ug/ml leupeptin, lug/ml aprotinin. Each 2.2 ml elution fraction was collected directly into 0.75 ml 0.5M HEPES, pH 7.0. Column fractions were subjected to the solubilized binding assay. FIG. 8 illustrates a column profile of elution of OCT binding protein from an MVIIA OCT affinity column.

At each stage in the purification, the amount of OCT binding protein present was determined by the amount of [$^{125}$I]MVIIA bound to the membrane material. The values measured, expressed in pmoles of binding protein and percent of total OCT binding protein in the synaptosomal membranes are given at the left in Table 3. The total amount of protein in the fractionated material, expressed in ng protein and percent total, is shown in the middle columns in this table. The specific binding activity of the purification fractions are determined from pmol OCT-binding/protein ratios, and are given at the right in the table. From these specific activity values, the degree of purification was calculated.

EXAMPLE 7

Inhibition of Ionic Currents

A. N1E 155 Cells

Ionic currents through calcium channels were examined in cells that were voltage-clamped by a single patch-clamp electrode. These whole-cell patch-clamp studies were performed mainly on N1E115 mouse neuroblastoma cells, although a variety of cell types have been examined.

Most current measurements were obtained using a bath saline that allowed examination of the calcium currents in the absence of other ionic currents. These solutions contained 80 mM NMDG (as a sodium replacement), 30 mM TEACl (to block potassium currents), 10 mM BaCl, (as a charge-carrier through the calcium channels), and 10 mM HEPES at pH 7.3. Some solutions also contained 2 mM quinidine (to block potassium currents) and 3 $\mu$M tetrodotoxin (to block sodium currents). Normal bath saline was (mM): 140 NaCl, 10 glucose, 3 KCl, 2 $CaCl_2$, 1 $MgCl_2$, 10 mM HEPES pH 7.3. Intracellular solutions contained 150 mM CsCl, 0.5 mM $CaC_2$, 5 mM EGTA, 5 mM $MgCl_2$, 2 mM $K_2ATP$ at pH 7.3–7.4. Bath saline and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2-5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 0.1 kHz; in all cases data was filtered at a frequency at most 1/5 of the sampling rate to avoid aliasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically $-100$ mV) to test potentials that ranged from $-60$ mV to $+20$ mV in 10 mV increments. The cell was held at the holding potential for 5 seconds between pulses. Protocols starting from other holding potentials usually covered the same range of test potentials.

B. Current Inhibition Measurement

FIG. 9 shows calcium current traces from an N1E-115 mouse neuroblastoma cell. The figure is read from left to right, with downward deflections of the trace indicating positive current flowing into the cell. Currents were elicited by a voltage step from 100 mV to $-10$ mV. The cell was bathed in saline with sodium replaced by NMDG and 10 mM Ba instead of 2 mM Ca. Potassium currents were blocked by TEA in the bath and Cs in the pipet solution.

The control current trace, labeled A, was measured in the presence of 1 $\mu$M nifedipine, a calcium channel blocker which has no effect on OCT-affected calcium currents. The three traces in FIG. 9, labeled B-C, show decreasing calcium currents, with increasing GVIA · OCT peptide concentrations of 10 nM (B), 50 nM (C), and 200 nM (D).

C. Inhibition of Synaptic Transmission in Hippocampal Slices

Excitatory post-synaptic potentials (EPSP's) and inhibitory post-synaptic potentials (IPSP's) recorded from hippocampal slices are a measure of transmitter release and, therefore, may be used to assess the function of central presynaptic VSCC's.

Normal solution was bicarbonate and phosphate buffered saline (mM) 124 NaCl, 26 NaHCO$_3$, 1.25 NaH$_2$PO$_4$, 5 KCl, 2 CaCl$_2$, 1 MgSO$_4$, 10 glucose. All solutions were continuously oxygenated. A low calcium, high magnesium solution used to block neurotransmitter release consisted of the above solution but with 0.1 mM CaCl$_2$ and 6mM MgSO$_4$.

Rats were killed by guillotine. The brain was quickly exposed and the cerebellum was severed and cerebrum hemisected by scalpel in the skull. Cerebral halves were dropped into cold, oxygenated saline. Each half was then retrieved, placed in wet (with saline) filter paper, the hippocampus dissented out and placed in fresh cold, bubbled saline. Both hippocampi were placed on wet filter paper mounted on a tissue chopper (McIlwain) and 400 micron sections were cut. Sections were removed from the blade using a wet paintbrush and replaced in cold saline. Slices were then collected with a pipet and placed on filter paper resting on saline in a humid, oxygenated chamber. Slices were maintained in this chamber for at least one hour before use, and remained viable for many hours.

Pipets were made from omega-dot glass (internal filament for ease of filling). Those used for extracellular recording were filled with 3M NaCl and were typically 1-5 Mohm in resistance. Intracellular electrodes were filled with either 3M KCl or 2M K-Acetate, and typically had resistances near 100 Mohm.

Field potentials and intracellular potentials were recorded using an Axoclamp 2A amplifier, the signal being further amplified by either a home-built amplifier, a Frequency Devices 902 Filter or a Brownlee 100 Instrumentation Amplifier. Data were filtered at 1 KHz by the Frequency Devices 902 filter and acquired by an IBM AT computer using pClamp software for analysis and storage on disk. Stimulation was via a WECO SC-100 Stimular isolation unit using stainless steel stimulating electrodes.

Hippocampal slices were pinned down to the tissue chamber, and stimulating electrodes were placed into the appropriate region of the slice, typically the stratum radiatum. Extracellular recording electrodes for field potentials were also placed into the stratum radiatum, while intracellular recording electrodes are placed in the stratum pyramidale. Constant-current stimulating pulses (usually 200 $\mu$sec) were applied once every 5 seconds. Stimulus was maintained throughout the experiment, even during periods of solution change or when no data was recorded, to avoid changes in response that might arise from rest or facilitation. Cells were also stimulated by current injection when intracellular recording was performed.

Tracings of electrophysiological extracellular recordings from a hippocampal slice are shown in FIG. 10. Trace A shows the excitatory postsynaptic potential (EPSP) in the absence of added OCT. Addition of MVIIA OCT (100-330 nM) to the bath caused a significant, dose-dependent decrease in the EPSP, as seen in traces B-D. Such a decrease reflects a decrease in synaptic transmission in the slice.

EXAMPLE 8

Inhibition of Neurotransmitter Release

A. ATP Neurotransmitter Release from Fish Synaptosomes

Synaptosomes were prepared substantially as described in Example 3A. The diluted synaptosome suspension from the final centrifugation step was pelleted at 30,400$\times$g for 15 min and resuspended in 1 ml of synaptosome buffer (with the inclusion, for some experiments, of 1% BSA to enhance stability of the synaptosomes). This final synaptosome preparation was stored at 0° C. and used for ATP release experiments within 30 hours. Storage for longer periods resulted in the almost complete loss of depolarization-dependent ATP release activity.

Luminometry was performed according to published method (Morel, Schweitzer). Into a 5 ml polypropylene test tube were mixed 465 $\mu$l synaptosome buffer, 5 $\mu$l of 5 $\mu$g/ml luciferin in PSB, 20 $\mu$l firefly lantern extract (1 Sigma FLE-50 bottle reconstituted in 1 ml PSB and spin-dialyzed through 3 ml of Sephadex G-25 pre-equilibrated in PSB), 5 $\mu$l 100 mM CaCl$_2$, and 5 $\mu$l synaptosome suspension (5-7 mg/ml protein, excluding BSA). The tube was placed in the chamber of a custom-built luminometer and the light output produced by extracellular ATP was continuously monitored by a chart recording of the voltage generated by the photomultiplier tube. Exocytotic release of ATP was evoked by injecting 0.5 ml of high K+ buffer (synaptosome buffer with equimolar replacement of Na+ by K+) into the reaction mixture in the luminometer.

ATP release was quantitated by comparing the peak heights or unknowns with the heights of peaks generated by ATP standards that were injected into each reaction mixture at the end of each trial. Over the range investigated, light output was linear with respect to the amount of ATP injected. $IC_{50}$ values, calculated from the dose-dependent ATP inhibition curves for synaptosomes prepared from electric organ of *Ommata discopyge*, were 10 nM for MVIIA and 130 nM for GVIA OCT peptides.

B. Amino Acid neurotransmitter release from rat brain slices

Male Sprague-Dawley rats were lightly anesthetized with ether, decapitated, and the brains removed to ice cold oxygenated basal medium (in mM: NaCl; 118, KCl, 4.8; $CaCl_2$, 1.3; $MgSO_4$, 1.2; $KH_2PO_4$, 1.2; qlucose, 11). Hippocampus and cerebral cortex were further dissected from the brain and slices (300-400 μm thick) were prepared using a McIlwain Tissue Chopper at 4 degrees. Each slice was preincubated at 37 degrees for 15 minutes. Buffer was then replaced with an equal volume of either basal medium or stimulation medium (in mM: NaCl; 88, KCl, 30; $CaCl_2$, 1.3; $MgSO_4$, 1.2; $KH_2PO_4$, 1.2; glucose, 11). Incubation was then continued for 15 minutes. Tubes containing slices were then centrifuged for 1 minute in a Beckman Microfuge. The supernatants were collected and heated for 10 minutes at 100 degrees. Aliquots (20ul) were used for analysis of amino acid content using pre-column derivatization with o-phthalaldehyde followed by HPLC as described by Newcomb.

Figure 11A:
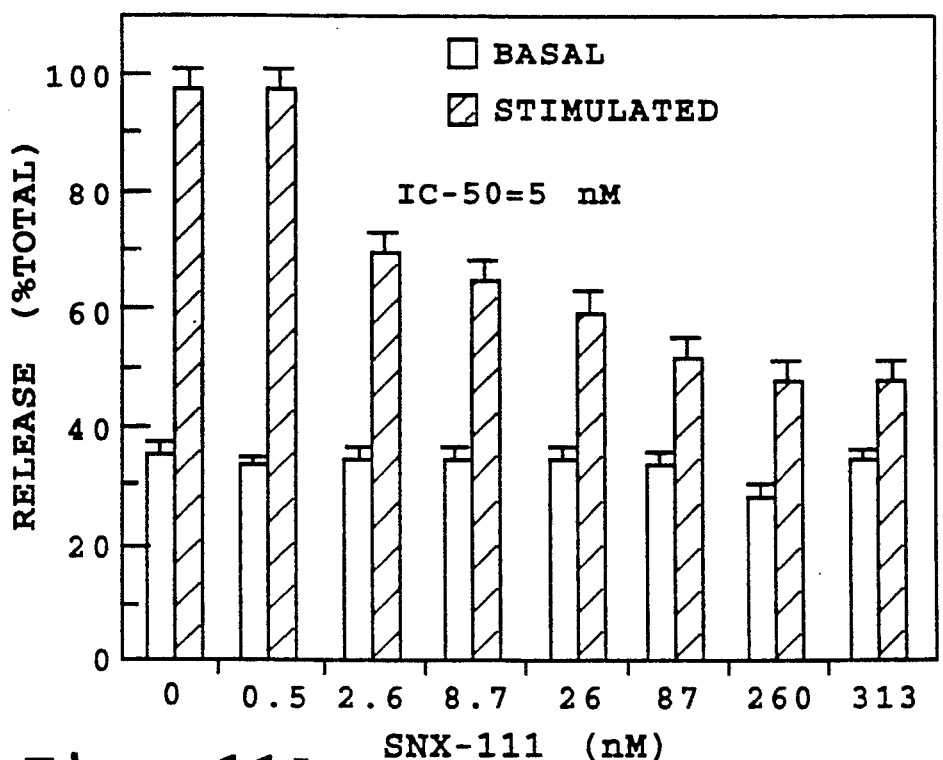
FIGS. 11A and B show the dose-dependent inhibition of potassium-stimulated [³H]Norepinephrine release by MVIIA (SNX-111), and the inhibition of potassium-stimulated release of glutamate and GABA by MVIIA (SNX-111), respectively.
Figure 11B:
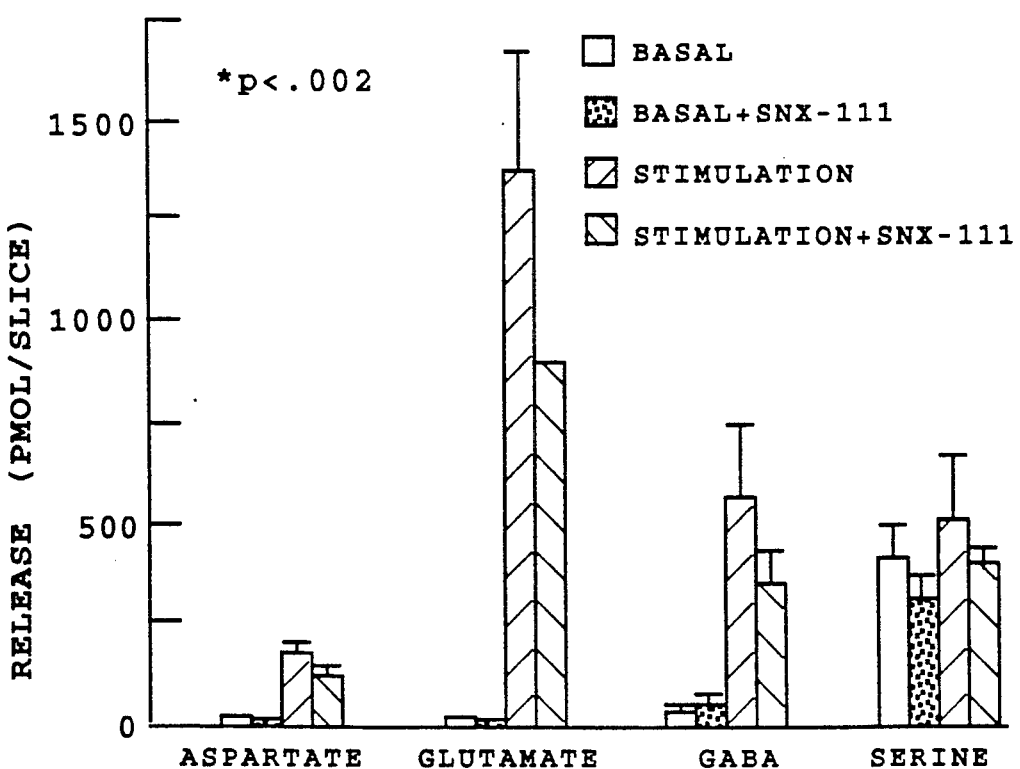

FIG. 11B shows the effect of MVIIA OCT on K-stimulated release of amino acid neurotransmitters (Aspartate, GABA, glutamate) contrasted to effects on serine, which is not a neurotransmitter. Significant reductions in the amount of GABA and glutamate were observed.

C. [$^3$H]Norepinephrine release from rat hippocampal slices

Male Sprague-Dawley rats were lightly anesthetized with ether, decapitated, and the brains removed. The hippocampi were then dissected free of cerebral cortex and rinsed with room temperature oxygenated uptake buffer (0.1% bovine serum albumen (BSA)in mM: NaCl, 123, KCl, 4.8; $CaCl_2$, 1.2; $MgSO_4$, 1.2; $KH_2PO_4$, 1.2; glucose, 11; $NaHCO_3$, 25). Slices (400 uM thick) were made using a McIlwain Tissue Chopper and were immediately transferred to room temperature uptake buffer. Slices were then distributed to individual wells of a 96-well plate (Dynatech) containing 0.1 ml uptake buffer per well. [3H]Norepinephrine (1 uCi/ml) diluted in uptake buffer containing 1 mM ascorbate and test compound was then added to each well. Incubation was at 37 degrees for 30 minutes in a humidified, 5% $CO_2$ incubator. Bathing buffer was then removed and slices washed two times for 11 minutes each with basal buffer containing appropriate test compound (basal buffer: 0.1% BSA in mM:NaCl, 123, KCl, 5.0; CaCl:, 0.4; $MgSO.$, 1.2; $KH_2PO_4$, 1.2; glucose, 11; $NaHCO_3$, 25). Each slice was then incubated for 15 minutes in 0.1 ml of basal buffer. This buffer was then removed for measurement and replaced by 0.1 ml stimulation buffer (0.1 BSA in mM:NaCl, 97, KCl, 30; $CaCl2$, 0.4; $MgSO_4$, 1.2; $KH_2PO_4$, 1.2; glucose, 11; $NaHCO_3$, 25) for 15 minutes. Stimulation buffer was then removed for measurement of radioactivity. Radioactivity remaining in each slice was determined. Data Were normalized to total cpm of radioactivity per slice: total radioactivity = S + B + slice, where S is the amount Of radioactivity present in the stimulation buffer, and B is the amount of radioactivity present in the basal buffer. Percent release = $[100/(S_0 - B_0)](S_i - B_i)$, where $_0$ refers to condition at time = 0, and $_i$ refers to condition at end of reaction time.

EXAMPLE 10

Mouse Shaking Test

Male Swiss-Webster mice were given intracerebroventricular (ICV) injections of the OCTs MVIIA, GVIA, and SVIA, or its vehicle at doses between 0.01-10.0 ug/animal. During the ICV injection the animal was unanesthetized, using a method previously described (Haley and McCormick, 1956). Animals were observed for the presence or absence of shaking behavior 15 minutes following injection. The percentage of animals exhibiting this behavior is shown in Table 9.

TABLE 9

| OCT | dose | n | percent "shakers" |
|---|---|---|---|
| vehicle | — | 100 | 4 |
| MVIIA | .01 | 30 | 32.5 |
|  | .03 | 60 | 38.6 |
|  | .1 | 60 | 61.4 |
|  | .3 | 50 | 80.0 |
|  | 1.0 | 10 | 100 |
| GVIA | .01 | 10 | 20.0 |
|  | .03 | 30 | 60.0 |
|  | .1 | 30 | 63.0 |
|  | .3 | 10 | 90.0 |
| MVIIB | .03 | 10 | 10 |
|  | .1 | 10 | 70 |
|  | .3 | 10 | 70 |
|  | 1.0 | 10 | 100 |
| RVIA | .3 | 10 | 0 |
|  | 1.0 | 10 | 0 |
|  | 3. | 10 | 50 |
|  | 10. | 10 | 60 |
| SVIA | .01 | 10 | 0 |
|  | .03 | 10 | 5.0 |
|  | .1 | 20 | 0 |
|  | .3 | 20 | 0 |
|  | 1.0 | 20 | 10 |
|  | 3.0 | 30 | 13.3 |
|  | 10.0 | 10 | 10 |
| TVIA | .1 | 10 | 20 |
|  | .3 | 10 | 40 |
|  | 1.0 | 10 | 80 |
|  | 3.0 | 10 | 100 |

EXAMPLE 11

Reduction in Anatomical Damage: 1

A. Global Ischemia

Global ischemic damage was examined in the gerbil model, according to standard procedures (Kirino). Male mongolian gerbils (*Meriones unguiculatus*, Tumblebrook Farm, West Brook field, Mass.) weighing 50-80 g were anesthetized in a small chamber with 4% halothane carried by 70% nitrous oxide (0.44 L/min) and 30% oxygen (0.19 L/min). They were then maintained throughout surgery with 2% halothane by placing their noses through a hole in a rubber dam on a gas delivery tube. Using aseptic techniques, both common carotid arteries were exposed, dissected free of surrounding tissue, and occluded with microvascular clamps approximately 3 to 4 mm above the clavicle. The occlusions were maintained for 8 minutes, timed while both arteries were occluded. There was generally a period of approximately 1 minute between clamping of each of the two arteries, and approximately 4 seconds between unclamping them. After the clamps were removed, the skin was sutured shut and anesthesia discontinued.

During or after the occlusion, an intracerebroventricular (ICV) injection aimed at the lateral ventricle was made. To accomplish this, a 10 microliter Hamilton syringe with a 27 gauge needle was filled with injectate by backloading to assure the absence of air in the system. A stiff plastic sleeve was slipped onto the needle so that 3.5 mm of the needle protruded past the sleeve. The skull around the bregma was exposed, a distance of 1.1 mm left of the midline was measured with a compass, and a distance of 0.4 mm posterior to bregma was approximated by eye. The needle tip was held perpendicular to the skull and inserted through it at that point by applying gentle pressure while twisting. It was advanced until the sleeve abutted the skull, and 5 microliters of injectate was infused over a period of approximately 3 sec. The skin was then sutured shut. Occluded animals received either drug or its vehicle. Injected, unoccluded controls were anesthetized, and received the ICV injection only.

B. Histological Examination of gerbil brains

Animals were anesthetized with $CO_2$. The chest cavity was opened and the animal was perfused through the heart with approximately 3 milliliters of phosphate-buffered saline (PBS; 0.10M sodium phosphate: 0.15M sodium chloride) containing heparin (10 Units/ml), followed by approximately 10 ml of Zamboni's fix (15% (vol/vol) picric acid 4% (wt/vol) paraformaldehyde in 0.1M phosphate buffer pH 7.4. Brains were removed and left immersed in the same fixative for several hours.

Brains were blocked just posterior to the optic chiasm and posterior to the mammillary bodies. They were the placed in 10% (wt/vol) sucrose in PBS overnight at 4i. The block containing the hippocampus was frozen with liquid Freon onto a cryostat chuck using Tissue-Tek$^R$ O.C.T. embedding medium for frozen tissue specimens (Miles Inc., Elkhart, Iowa) Sections 10 microns in thickness were cut. Series of 5 sections were collected, with each series approximately 100 microns apart, until the relevant part of the hippocampus was obtained (40-50 sections per brain). At least 8 sections per brain were stained with hematoxylin and eosin, substantially according to reported procedures.

Coverslips were then placed over the sections, using Permount TM as an adhesive. FIGS. 12A and 12B are low-power micrographs of qerbil hippocampus (CA) in animals after ischemia, after infusion of MVIIA OCT (13A) or after drug vehicle (12B). The arrows in the figures indicate the approximate borders of the CA. At higher power, cells in the drug-treated ischemic animals appear normal (FIG. 14C), whereas damage is apparent in the ischemic animals receiving vehicle alone (FIG. 13D). Another example of complete drug protection is seen in FIG. 13E, and an example of partial protection is seen in FIG. 13F, where there are a small number of damaged cells.

Sections, such as those seen in FIGS. 12 and 13, were viewed and scored by an investigator having no knowledge of the treatment of any particular sample. Ischemic damage was scored in the CA-1 region of the hippocampus. Damage was generally seen as pink (eosinophilic) cytoplasm and shrunken, dark blue nuclei. Scoring was as described below:

| Score | Observation |
|---|---|
| 0 | No damaged cells were apparent. |
| 1 | Less than 25% damaged cells in a CA field, or damage was restricted to the extreme edges of the CA 1 region. |
| 2 | Approximately 50% damaged cells in a CA 1 field, or damage to less than half the length of CA 1. |
| 3 | Damaged cells outnumber normal cells to a maximum of 75%, with damage extending throughout most of CA 1. |
| 4 | Complete damage to CA 1, with fewer than 25% normal cells surviving. |

The extent of anatomical damage in ischemic animals treated with MVIIA or GVIA OCT or receiving vehicle alone (control), based on the above scoring system, is given in Table 10 below. The peptide was administered by ICV infusion during the eight minutes of occlusion, at a total dose indicated in the table below. As seen, the extent of damage in the higher-dose MVIIA OCT treated animal was only 25% of that in untreated animals. The GVIA peptide also produced more than a 50% reduction in damage, and the lower dose was near maximal effectiveness.

TABLE 10

| Treatment | N | Mean score (S.E.M) | Percent Damage |
|---|---|---|---|
| Vehicle | 20 | 3.1 (.32) | 100% |
| 0.02 ug MVIIA | 4 | 1.9 (.83) | 61% |
| 1.0 ug MVIIA | 18 | 0.8 (.09)*** | 25% |
| 0.02 ug GVIA | 3 | 1.3 (.33)* | 42% |
| 0.1 μg GVIA | 11 | 1.2 (.39)** | 39% |

*$p < .05$ compared to vehicle (Student's T-test)
**$p < .005$ compared to vehicle (Student's T-test)
***$p < .0005$ compared to vehicle (Student's T-test)

In a second treatment method, the OCT peptide was administered by ICV infusion 1 hour after the 8-min occlusion, at the same drug dosage level as indicated above. The anatomical damage in the presence and absence of drug, scored as above, is given in Table 11 below. A comparison of the data in Table 10 indicates little loss of protective effect at a comparable dose (0.1 μg) when the drug is administered 1 hour after the ischemic event (8 mn of occlusion).

TABLE 11

| Treatment | N | Mean score (S.E.M) | Percent Damage |
|---|---|---|---|
| Vehicle | 15 | 3.0 (.31) | 100% |
| 0.1 μg MVIIA | 16 | 0.9 (.13)*** | 30% |
| 0.3 μg MVIIA | 3 | 0.7 (.17)** | 23% |

**$p < .005$ compared to vehicle (Student's T-test)
***$p < .0005$ compared to vehicle (Student's T-test)

C. Global Ischemia in Rats

Global ischemic damage was examined in the rat brain model, employing the four-vessel occlusion method of Pulsinelli and Brierly (Pulsinelli) for introducing temporary global ischemia in rats. Although the two carotid arteries supply blood to the forebrain, their occlusion alone has only moderate effects on forebrain blood flow because the posterior communicating arteries allow blood to be shunted from the brainstem blood supply, which is fed by the two vertebral arteries. Therefore, in order to effect severe forebrain ischemia, all four vessels must be occluded. The procedure used allows ischemia to be produced in conscious animals, by closing surgically implanted clamps, and therefore avoid possible interactions with drug treatment. The procedure was modified to allow carotid occlusion without the need for reopening a skin wound in conscious animals.

Surgery was performed to permanently occlude both vertebral arteries and to implant an arterial clasp to allow temporary occlusion of the carotid arteries at a later time. Under sodium pentobarbital anesthesia (60 mg/kg) male Fisher 344 rats were placed in a stereotaxic holder and the first cervical vertebra was exposed with the aid of a dissecting microscope. The vertebral arteries were occluded through the alar foramina with a thermocautery device and the skin closed with wound clips. The animal was placed on its back and the carotid arteries were carefully dissected free of the surrounding nerves and vessels under the microscope. The loose end of the Silastic loop of the clasp was passed behind the artery and put through the open side of the clasp and secured as for the other end. This was then repeated for the other carotid. The clasps were tied into the skin with 3-0 suture as the skin was closed so as to externalize the ends of the loop.

Ischemia was produced 4 days after surgery. To occlude the carotid arteries, the animal was held by lightly pinching the skin at the back of the neck and the ends of each loop were pulled out and secured with a bulldog clamp. At the end of the 15 min. occlusion, the clamps were removed to allow reperfusion. An effective occlusion causes the animal to lose its righting response (RR) within about 1 min. of occlusion. When the animal does not lose the RR or regains it during occlusion, the loops are pulled tighter to assure complete carotid occlusion. Animals that do not lose their RR are eliminated from the study, because this suggests that there is still significant cerebral blood flow.

Neuropathological analysis (see below) of such animals confirms this because the damage is less than in animals that do lose their RR. Some animals right themselves once or twice during the occlusion but immediately lose the RR again, and are not eliminated from the study. An animal that rights itself and remains up is eliminated.

Immediately following reperfusion, rats were anesthetized with halothane (as for gerbils) and 0.3 μg MVIIA OCT in 5 μl saline (n=7) or saline alone (n=5) was injected into the lateral ventricle as for gerbils. The coordinates were 1.2 mm left of midline and 0.5 mm posterior to bregma. Rectal temperature was monitored from just before occlusion until the end of the day.

Neuropathologic analysis was conducted in a manner similar to that described for gerbils, with the results shown in Table 1

TABLE 12

| Effect of OCT MVIIA on Hippocampal Damage Produced in Rats by 4-VO (15 min. duration) | | |
|---|---|---|
| Treatment | N | Mean Score (SEM) |
| vehicle | 4 | 3.6 (0.38) |
| MVIIA OCT (0.3 μg) | 5[a] | 1.2 (0.36)** |

[a]Animals given CmTx ICV were included in the study only if they exhibited characteristic shaking behavior.
p < .005, unpaired Student's t test.

As seen from the data, treatment With MVIIA OCT reduced anatomical damage to about ⅓ that seen in the absence of peptide treatment.

EXAMPLE 12

Protection Against Loss of Functional Activity

A. Hyperactivity

One common sequence of cerebral ischemia is hyperactivity, which can be seen as pacing behavior within a few hours of occlusion and can be measured up to several days later. Hyperactivity was quantitated with Automex activity monitors (Columbia Instruments, Columbus, Ohio), which record perturbations of radiofrequency field. Gerbils were tested individually in 17×27-cm plastic cages for 60 min, with cumulative activity counts recorded every 15 min for statistical analysis. Baseline activity was measured before surgery to ensure comparability of the different treatment groups on this measure.

Figure 14:
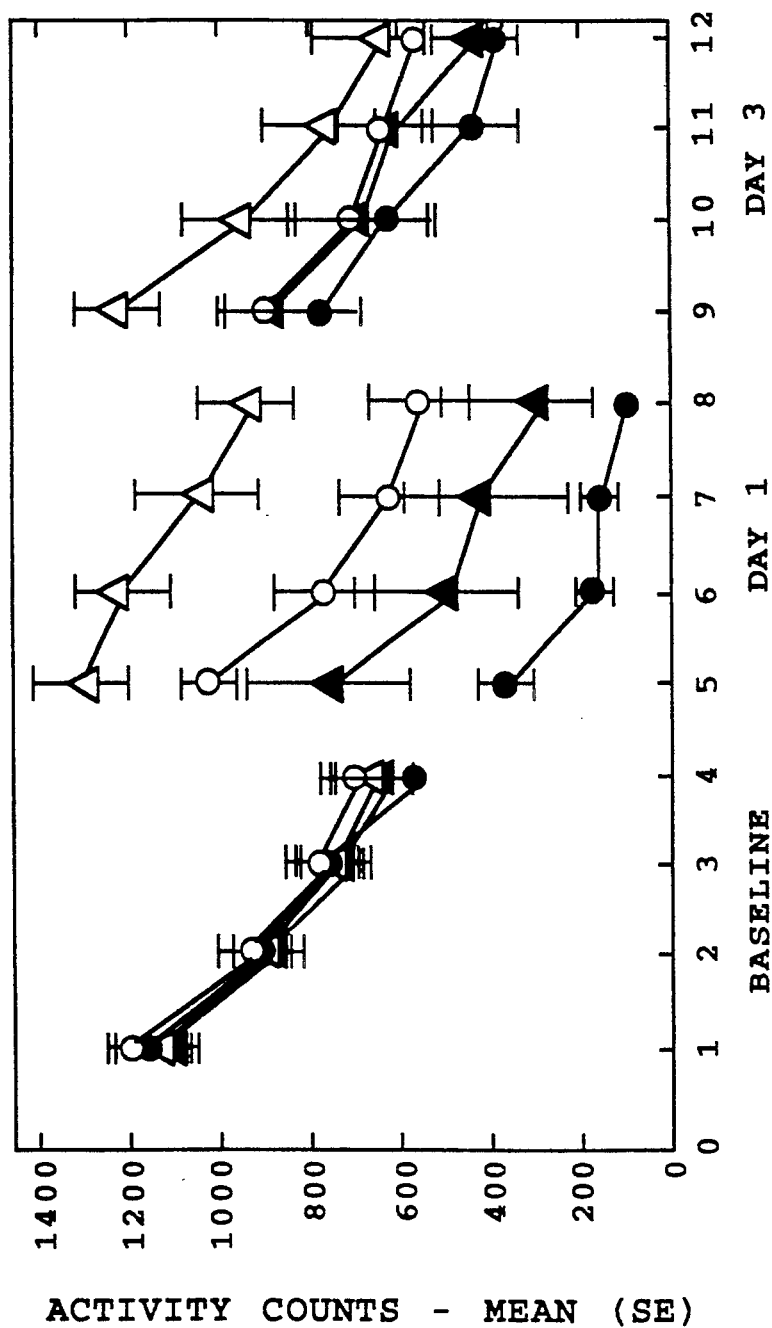
FIG. 14 plots the changes in spontaneous motor activity animals which were (a) unoccluded and untreated (open circles), (b) unoccluded and treated with MVIIA peptide (closed circles), (c) occluded but untreated (open triangles), and (d) occluded and treated with MVIIA peptide (closed triangles).

The results of the tests are plotted in FIG. 14. The downward slope in each test curve is due to the decrease in activity over the four 15 minutes intervals of the test (1–4 for baseline, 5–8 at day 1, and 9–12 at day three), as the animal becomes more familiar with the test environment. Occlusion alone (open triangles) produced a significant rise in activity level over baseline levels 1 day after occlusion, and an elevated activity level was observed over a three-day period, indicating permanent behavioral damage. Non-occluded control animals receiving ICV administration of vehicle (open circles) remained at baseline activity levels through the test period. OCT peptide itself, in the absence of ischemia (solid circles) reduces activity, and this effect persists slightly even at three days. Occluded animals which had been treated with OCT MVIIA (solid triangles) showed lower-than baseline values at 1 day, apparently reflecting the reduced activity produced by the peptide alone. At three days, treated animals showed near-normal levels of activity, indicating that the OCT peptide treatment provided protection against ischemia-induced hyperactivity.

B. Spontaneous Alternation

Because the predominant neuropathological consequence of the type of ischemia used here is hippocampal damage (Example 11) which is known to produce deficits in spatial learning and memory, a test of recent (working) memory in maze performance were employed. This test uses a Y maze.

Gerbils were tested in a Y maze, in which the animal is placed in the base of the stem of the maze, and when the animal enters an arm, a door is shut behind it. After 5 sec, the gerbil is returned to its home cage for an intertrial interval (ITI) of 2 to 12 min. At the end of that interval the gerbil is run in the maze again in the same way. Most normal animals will alternate, that is, will enter the arm that was not entered on the first trial. Occasionally an animal did not enter an arm within about 1 min. because it had a seizure, so it was eliminated from that test.

Because individual experiments include too few animals per group to allow meaningful statistical evaluation of the data, the results were combined for all experiments in which there was good evidence of protection by drug treatment against hippocampal damage (Example 11). Only experiments with positive results were combined to determine if the anatomical protection was associated with behavioral protection.

Results of the spontaneous alternation tests are summarized in Table 13 for experiments in which there was anatomical protection from doses of at least 0.1 μg of either compound. A chi square test on the combined data was significant at p <0.01 Combining treatment groups to examine each factor separately (e.g., all occluded vs. all unoccluded, regardless of drug treatment) indicated that each was significant by chi square at p <0.05; that is, (a) ischemia caused worse performance and (b) the level of performance was largely restored in treated animals.

TABLE 13

| | | No. Gerbils Alternating (Y) or Repeating (N) Experiments | | | | | | | | |
|---|---|---|---|---|---|---|---|---|---|---|
| | | 3 | | 4 | | 5 | | 6 | | Combined |
| | | Y | N | Y | N | Y | N | Y | N | Y | N |
| Ischemia | Drug* | | | | | | | | | | |
| No | No | 9 | 3 | 2 | 2 | 3 | 3 | 6 | 2 | 20 | 10 |
| | Yes | — | — | 4 | 0 | 5 | 1 | 4 | 0 | 13 | 1 |
| Yes | No | 2 | 6 | 4 | 4 | 4 | 4 | 3 | 4 | 13 | 18 |
| | Yes | 4 | 3 | 5 | 2 | 7 | 1 | 7 | 4 | 23 | 10 |

*Drug doses are from 0.1 to 0.3 μg of MVIIA or GVIA.

Although the invention has been described with respect to particular treatment methods and composition, it will be apparent to those skilled that various changes and modifications can be made without departing from the invention.

It is claimed:

1. A method of screening compounds for use in reducing neuronal damage resulting from ischemic conditions in a human, comprising
    measuring the binding affinity of the compounds being screened by competitive displacement of omega conotoxin MVIIA from an isolated synaptosomal omega-conotoxin binding protein having a molecular weight of about 210 kilodaltons as measured by sodium dodecyl sulfate polyacrylamide gel electrophoresis, and
    selecting a compound if its binding affinity to the binding protein is sufficient to produce a displacement of said omega conotoxin MVIIA, wherein said displacement is at least as great as that of an omega conotoxin selected form the group consisting of MVIIA, MVIIB, GVIA, GVIIA and RVIA omega conotoxins.

* * * * *